US012056874B2

(12) United States Patent
Zhang

(10) Patent No.: US 12,056,874 B2
(45) Date of Patent: Aug. 6, 2024

(54) DEVICE, PROCESS AND SYSTEM FOR DIAGNOSING AND TRACKING OF THE DEVELOPMENT OF THE SPINAL ALIGNMENT OF A PERSON

(71) Applicant: CONOVA MEDICAL TECHNOLOGY LIMITED, Hong Kong (CN)

(72) Inventor: Teng Zhang, Hong Kong (CN)

(73) Assignee: CONOVA MEDICAL TECHNOLOGY LIMITED, Hong Kong (CN)

( * ) Notice: Subject to any disclaimer, the term of this patent is extended or adjusted under 35 U.S.C. 154(b) by 400 days.

(21) Appl. No.: 17/622,723

(22) PCT Filed: Jun. 24, 2020

(86) PCT No.: PCT/CN2020/098157
§ 371 (c)(1),
(2) Date: Dec. 24, 2021

(87) PCT Pub. No.: WO2020/259600
PCT Pub. Date: Dec. 30, 2020

(65) Prior Publication Data
US 2022/0254018 A1 Aug. 11, 2022

(30) Foreign Application Priority Data
Jun. 24, 2019 (HK) .................. 19125755.9

(51) Int. Cl.
*G06K 9/00* (2022.01)
*A61B 5/00* (2006.01)
(Continued)

(52) U.S. Cl.
CPC .......... *G06T 7/0012* (2013.01); *A61B 5/4561* (2013.01); *A61B 5/7267* (2013.01);
(Continued)

(58) Field of Classification Search
CPC . G06T 2207/30012; G06T 2207/10116; G06T 19/006; G06T 7/0012;
(Continued)

(56) References Cited

U.S. PATENT DOCUMENTS

| 11,331,039 B2 * | 5/2022 | Matsumoto .......... A61B 5/0073 |
| 2002/0196966 A1 | 12/2002 | Jiang et al. |

(Continued)

FOREIGN PATENT DOCUMENTS

| CN | 103607947 A | 2/2014 |
| CN | 109464148 A | 3/2019 |

(Continued)

OTHER PUBLICATIONS

M. Levine al et. "Automatic vertebrae localization in spine CT: a deep-learning approach for image guidance and surgical data science", Proc. SPIE 10951, Medical Imaging 2019: Image-Guided Procedures, Robo Interventions, and Modeling, 109510S (Mar. 8, 2019) (Year: 2019).*

(Continued)

*Primary Examiner* — Alex Kok S Liew
(74) *Attorney, Agent, or Firm* — JCIP; Joseph G. Chu; Jeremy I. Maynard

(57) ABSTRACT

A process operable using a computerized system for providing one or more output images of the spinal region of a subject for which anatomical landmarks applicable for clinical assessment are labeled in a pre-trained neural network (120a, 120b) for clinical assessment of malalignment of a spine of a subject, the computerized system (100a, 100b) including an image data acquisition device (110a), a pre-trained neural network (120a, 120b) and an output module (140a) operably interconnected together via a communication link, said process including the steps of (i) by an image (Continued)

data acquisition device (110a,), acquiring one or more data input sets indicative of the spinal region of a subject, wherein each data input set of the one or more data input sets is indicative of an optical image of said subject at one or more corresponding postures of the subject; (ii) in a pre-trained neural network (120a,120b), providing labels to anatomical landmarks of said one or more data input sets each of which is indicative of said optical image of the subject at said one or more postures of the subject acquired during step (i) so as to provide one or more optical output images for subsequent clinical assessment of the spine of said subject, wherein the pre-trained neural network (120a, 120b) has been pre-trained utilising one or more training data input sets corresponding to one or more predetermined postures of training subjects acquired from a plurality of training subjects, wherein said one or more predetermined postures are postures utilized for clinical assessment of malalignment of the spine of a subject; wherein the anatomical landmarks of the spine of said one or more training data input sets acquired from said plurality of training subjects have been pre-labeled by at least one clinician; and wherein the one or more postures of said subject for which the one or more data input sets of the subject acquired during step (i) correspond to one or more of said predetermined postures; and (iii) displaying by the output module (140a), the one or more optical output images of the spinal region of said subject having said labels provided thereto by the pre-trained neural network (120a,120b), for clinical assessment.

20 Claims, 7 Drawing Sheets

(51) Int. Cl.
 G06T 7/00 (2017.01)
 G16H 30/20 (2018.01)
 G16H 50/20 (2018.01)
(52) U.S. Cl.
 CPC ............. *G16H 30/20* (2018.01); *G16H 50/20* (2018.01); *G06T 2207/10028* (2013.01); *G06T 2207/10088* (2013.01); *G06T 2207/10116* (2013.01); *G06T 2207/30012* (2013.01)
(58) Field of Classification Search
 CPC ............. G06T 2207/30204; G06T 7/33; G06T 2200/24; G06T 2207/10028; G06T 2207/20101; G06T 2207/30008; G06T 2210/41; G06T 7/73; G06T 2207/10081; G06T 2207/10088; G06T 2207/30004; G06T 2207/30036; G06T 3/40; G06T 17/00; G06T 19/003; G06T 2207/10072; G06T 2207/30052; G06T 7/30; G06T 7/60; G06T 7/70; G06T 19/00; G06T 7/38; G06T 2207/10016; G06T 2207/20084; G06T 2207/20081; G06T 7/11

See application file for complete search history.

(56) References Cited

U.S. PATENT DOCUMENTS

2020/0205900 A1\* 7/2020 Buckland ................ G06V 10/82
2021/0118134 A1\* 4/2021 Ferrantelli ........... G06V 10/776

FOREIGN PATENT DOCUMENTS

| CN | 109493334 A | 3/2019 |
|---|---|---|
| CN | 109886320 A | 6/2019 |
| WO | 2010018407 A1 | 2/2010 |

OTHER PUBLICATIONS

B. Aubert, C. Vazquez, T. Cresson, S. Parent and J. A. de Guise, "Toward Automated 3D Spine Reconstruction from Biplanar Radiographs Using CNN for Statistical Spine Model Fitting," in IEEE Transactions on Medical Imaging, vol. 38, No. 12, pp. 2796-2806, Dec. 2019 (Year: 2019).\*
International Search Report and Written Opinion of International Searching Authority for International Application No. PCT/CN2020/098157.

\* cited by examiner

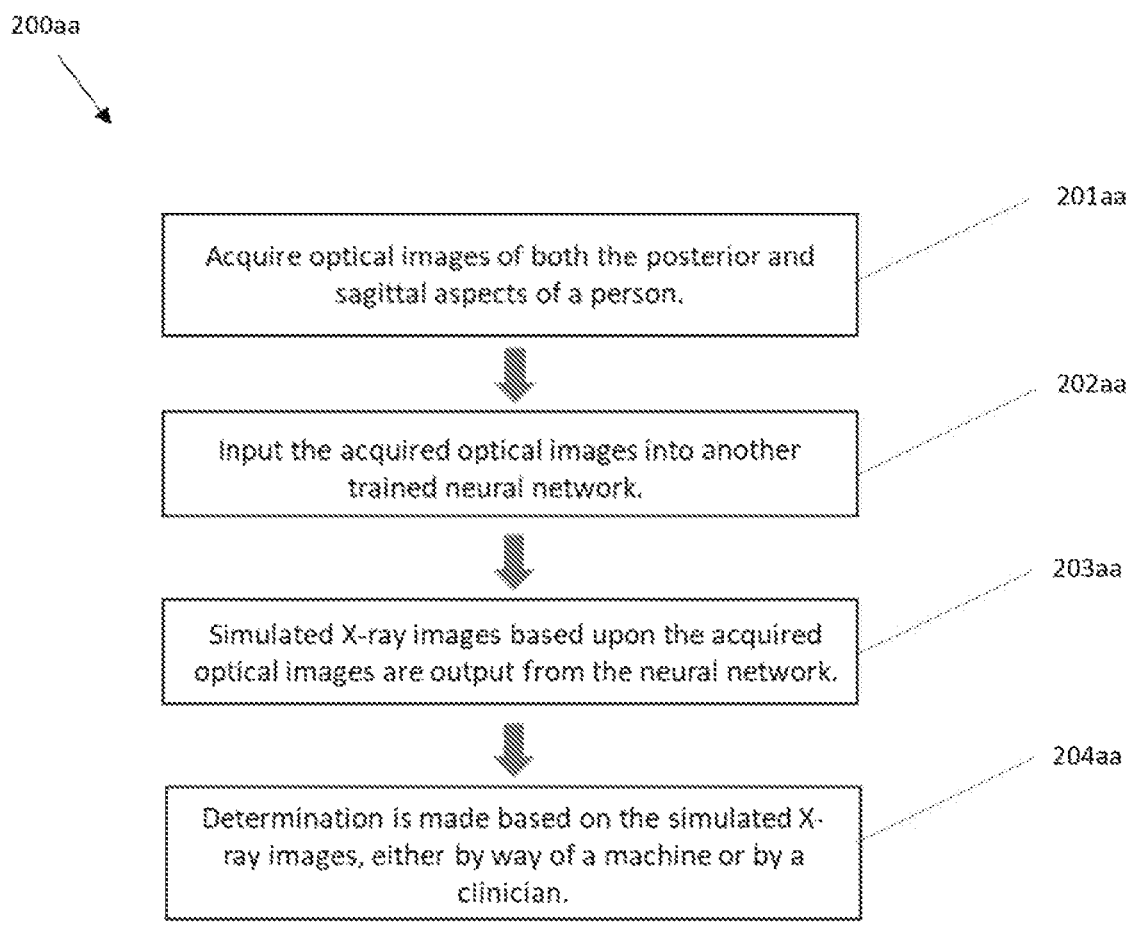
Figure 2a(ii)

DEVICE, PROCESS AND SYSTEM FOR DIAGNOSING AND TRACKING OF THE DEVELOPMENT OF THE SPINAL ALIGNMENT OF A PERSON

TECHNICAL FIELD

The present invention relates to a device, process and system for diagnosing and tracking of the development of the spinal alignment of a person. More particularly, the present invention provides a device, process and system for diagnosing and tracking of the development of the spinal alignments for patients suffering from spinal deformity.

BACKGROUND OF THE INVENTION

Spinal health is a crucial factor for the overall health of a person. The spine provides for key structural support to our body, and as such any disorders or abnormalities therein may lead to serious adverse effects to both the physical appearance and the cardiovascular, pulmonary and neural system of a person.

From a clinical background perspective, spine malalignment includes two patient cohorts:
(i) patients with scoliosis,
(ii) and patients with degenerative spinal disorders and deformity and possibly neck or back pain.

Scoliosis is typically considered as a 3-dimensional deformity characterized as an abnormal lateral curvature of the spine with or without sagittal malalignment. Its most common form occurs during adolescence, and is commonly known as adolescent idiopathic scoliosis (AIS). Based on the Hong Kong scoliosis school screening data (comprising of 78% of the total student population), at the time of writing, up to 2.2% of boys and 4.8% of girls have scoliosis. It is thus, the most common spine condition in the paediatric population.

Progression of AIS occurs with natural growth. Without prompt intervention, this deformity may deteriorate and result in cosmetic disfigurement, back pain and cardiopulmonary compromise in severe cases. Worsening of spine curvature may also cause stigmatization and poor self-esteem in such young children.

Further, at the other end of the spine malalignment spectrum, spinal disorders is now at the forefront of most spine practices due to improved medicine and expected quality of life of our elderly population.

The incidence is up to 32% in adults and 60% in the elderly [1-3]. Thus, as will be understood, back and/or neck pain can now be considered as the most common presenting symptom in many clinics and has tremendous financial and social burden on patients and healthcare [4, 5].

It has been identified as the leading global cause of disability in most countries in 2015 and a large percentage can be contributed to deformity [4].

As such, the impact of this disease is recognised globally to growing number of patients with back pain and deformity, there is an increased interest in improving our knowledge of its pathogenesis, of optimal corrective surgeries and on the impact on health-related quality of life.

Hence in the past decade, much effort has been made to determine ideal alignment parameters [6-9], fusion level selection, corrective techniques and instrumentation strategies [10-15].

OBJECT OF THE INVENTION

It is an object of the present invention to provide a device, process and system for diagnosing and tracking of the development of the spinal alignment of a person, which overcomes or at least partly ameliorates at some deficiencies as associated with the prior art.

SUMMARY OF THE INVENTION

In a first aspect, the present invention provides a process operable using a computerized system for providing one or more output images of the spinal region of a subject for which anatomical landmarks applicable for clinical assessment are labeled in a pre-trained neural network for clinical assessment of malalignment of a spine of a subject, the computerized system including an image data acquisition device, a pre-trained neural network and an output module operably interconnected together via a communication link, said process including the steps of:

(i) by an image data acquisition device, acquiring one or more data input sets indicative of the spinal region of a subject, wherein each data input set of the one or more data input sets is indicative of an optical image of said subject at one or more corresponding postures of the subject;

(ii) in a pre-trained neural network, providing labels to anatomical landmarks of said one or more data input sets each of which is indicative of said optical image of the subject at said one or more postures of the subject acquired during step (i) so as to provide one or more optical output images for subsequent clinical assessment of the spine of said subject, wherein the pre-trained neural network has been pre-trained utilising one or more training data input sets corresponding to one or more predetermined postures of training subjects acquired from a plurality of training subjects, wherein said one or more predetermined postures are postures utilized for clinical assessment of malalignment of the spine of a subject; wherein the anatomical landmarks of the spine of said one or more training data input sets acquired from said plurality of training subjects have been pre-labeled by at least one clinician; and wherein the one or more postures of said subject for which the one or more data input sets of the subject acquired during step (i) correspond to one or more of said predetermined postures; and (iii) displaying by the output module, the one or more optical output images of the spinal region of said subject having said labels provided thereto by the pre-trained neural network, for clinical assessment.

The pre-trained neural network may be further trained utilising one or more X ray images acquired simultaneously when the one or more data input sets are acquired from the plurality of training subjects, and wherein the neural network provides one or more simulated X ray images corresponding to the one or more acquired data input sets of the spinal region of the subject, having said labels provided thereto by the pre-trained neural network, for clinical assessment.

The pre-trained neural network may be further trained utilising one or more X ray images acquired simultaneously when the one or more data input sets are acquired from the plurality of training subjects, and wherein the neural network provides one or more simulated X ray images corresponding to the one or more acquired data input sets of the spinal region of said subject, having said labels provided thereto by the pre-trained neural network, and wherein said one or more simulated X ray images corresponding to the one or more acquired optical input images of the spinal region of said subject having said labels provided thereto are processed by a processing module, wherein said processing module provides for image analysis and calculations to the labelled images and provides analysis and clinical assessment of malalignment of a spine of said subject.

The image data acquisition device may be an optical image acquisition device, and wherein the data input sets are optical input images.

The optical image acquisition device may be a fixed CCD/CMOS camera installed in clinics or hospitals in a room or environment in which an input image is to be acquired.

the optical image acquisition device may be a built-in camera of a purpose specific mobile device or a mobile device.

The image data acquisition device may be a depth sensor, and the depth sensor is a depth camera.

The anatomical landmarks of the spine of said one or more training data input sets acquired from said plurality of training subjects may have been pre-labeled by two or more clinicians, wherein consensus is sought between said two or more clinicians. In the event consensus is not reached between said two or more clinicians, one or more further clinician pre-labels said one or more training data input sets until a consensus threshold is reached.

In a second aspect, the present invention provides a process operable using a computerized system for providing one or more output images of the spinal region of a subject for which anatomical landmarks applicable for clinical assessment are labeled for clinical assessment of malalignment of a spine of a subject, the computerized system including an input interface, a pre-trained neural network and an output module operably interconnected together via a communication link, said process including the steps of:
(i) acquiring one or more medical input images of a subject, wherein each medical input image of the one or more medical input images is an image of said subject at one or more corresponding postures;
(ii) in a pre-trained neural network, providing labels to anatomical landmarks of one or more medical input images of said subject at said one or more postures of the subject acquired during step (i) for providing one or more medical output images for subsequent clinical assessment of the spine of said subject which are input into a pre-trained neural network by a input interface;
   wherein the pre-trained neural network has been pre-trained utilising or more medical training images corresponding to one or more predetermined postures of training subjects acquired from a plurality of training subjects at one or more predetermined postures;
   wherein said one or more predetermined postures are postures utilized for clinical assessment of malalignment of the spine of said subject, and wherein the anatomical landmarks of the spine of said one or more medical training images acquired from the plurality of training subjects have been pre-labeled by at least one clinician; and
   wherein the one or more postures of said subject for which the one or more medical input images of the subject acquired during step (i) correspond to one or more of said predetermined postures; and
(iii) displaying by the output module, the one or more medical output images of the spinal region of said subject having said labels provided thereto by the pre-trained neural network, for clinical assessment.

The medical image may be selected from the group including CT (computer tomography) scans, X-ray, MRI (magnetic resonance imaging, CBCT (Cone beam computed tomography) or the like.

In a third aspect, the present invention provides a process operable using a computerized system for providing one or more images of the spinal region of a subject for which anatomical landmarks applicable for clinical assessment are labeled for clinical assessment of malalignment of a spine of a subject, the computerized system including an input interface, a pre-trained neural network and an output module operably interconnected together via a communication link, said process including the steps of:
(i) acquiring one or more medical input images of a subject, wherein each medical input image of the one or more medical input images is an image of said subject at one or more postures of said subject;
(ii) in a pre-trained neural network, providing labels to anatomical landmarks of one or more medical input images of said subject at said one or more postures of the subject acquired during step (i) for subsequent clinical assessment of the spine of said subject which are input into a pre-trained neural network by a input interface;
   wherein the pre-trained neural network has been pre-trained utilising or more medical training images corresponding to one or more predetermined postures of training subjects acquired from a plurality of training subjects at one or more predetermined postures
   wherein said one or more predetermined postures are postures utilized for clinical assessment of malalignment of the spine of said subject, and wherein the anatomical landmarks of the spine of said one or more medical training images acquired from the plurality of training subjects have been pre-labeled by a clinician; and
   wherein the one or more postures of said subject for which the one or more medical input images of the subject acquired during step (i) correspond to one or more of said predetermined postures; and
(iii) in a processor module, processing the one or more medical input images of the spinal region of said subject having said labels provided thereto by the pre-trained neural network by way of one or more rules-based assessment criteria based on the labelled anatomical landmarks so as to provide assessment data; and
(iv) displaying by the output module, said assessment data from step (iii) for clinical assessment.

The rules-based assessment criteria preferably is a clinical assessment criteria.

The clinical assessment criteria may be Cobb angle assessment

In a fourth aspect, the present invention provides a computerized system for providing one or more images of the spinal region of a subject for which anatomical landmarks applicable for clinical assessment are labeled for clinical assessment of malalignment of a spine of a subject, the computerized system including:
   an image data acquisition device, for acquiring one or more data input sets of the spinal region of a subject, wherein each data input set of the one or more data input sets i is indicative of an optical image of said subject at one or more corresponding postures of the subject;
   a pre-trained neural network, for providing labels to anatomical landmarks of said one or more data input sets indicative of the subject at said one or more postures of the subject acquired from the image data acquisition device for providing optical output images for subsequent clinical assessment of the spine of said subject, wherein the pre-trained neural network has been pre-trained one or more training data input sets corresponding to one or more predetermined postures of training subjects acquired from a plurality of training subjects, wherein said one or more predetermined postures are postures utilized for clinical assessment of malalignment of the spine of a subject; wherein the anatomical landmarks of the spine of said one or more training data input sets acquired from said plurality of training subjects have been pre-labeled by at least one clinician and;

wherein the one or more postures of said subject for which the one or more data input sets indicative of the subject is acquired correspond to one or more of said predetermined postures; and an output module, for displaying the one or more optical output images of the spinal region of said subject having said labels provided thereto by the pre-trained neural network, for clinical assessment.

The pre-trained neural network may be further trained utilising one or more X ray images acquired simultaneously when the one or more data input sets are acquired from the plurality of training subjects, and wherein the neural network provides one or more simulated X ray images corresponding to the one or more acquired data input sets of the spinal region of the subject, having said labels provided thereto by the pre-trained neural network, for clinical assessment.

The pre-trained neural network may be further trained utilising one or more X ray images acquired simultaneously when the one or more data input sets are acquired from the plurality of training subjects, and wherein the neural network provides one or more simulated X ray images corresponding to the one or more acquired data input sets of the spinal region of said subject, having said labels provided thereto by the pre-trained neural network, and wherein said one or more simulated X ray images corresponding to the one or more acquired optical input images of the spinal region of said subject having said labels provided thereto are processed by a processing module, wherein said processing module provides for image analysis and calculations to the labelled images and provides analysis and clinical assessment of malalignment of a spine of said subject.

The image data acquisition device may be an optical image acquisition device, and wherein the data input sets are optical input images.

The optical image acquisition device may be a fixed CCD/CMOS camera installed in clinics or hospitals in a room or environment in which the image is to be acquired.

The optical image acquisition device may be a built-in camera of a purpose specific mobile device or a mobile device.

The image data acquisition device may be a depth sensor. The depth sensor may be a depth camera.

The anatomical landmarks of the spine of said one or more training data input sets acquired from said plurality of training subjects may have been pre-labeled by two or more clinicians, wherein consensus is sought between said two or more clinicians. In the event consensus is not reached between said two or more clinicians, one or more further clinician pre-labels said one or more training data input sets until a consensus threshold is reached, The optical image acquisition device may further includes the output module. The output module is a visual display unit.

The optical image acquisition device may carry thereon a software executable thereon for communication with said neural network.

The optical image acquisition device may includes a user interface for guiding a user in respect of acquisition of said predetermined postures and the acquisition of images thereof.

In a fifth aspect, the present invention provides a computerized system for providing one or more images of the spinal region of a subject for which anatomical landmarks applicable for clinical assessment are labeled for subsequent clinical assessment of malalignment of a spine of a subject, the computerized system including:

an input interface for receiving one or more medical input images of a subject, wherein each medical input image of the one or more medical input images is an image of said subject at one or more corresponding postures, a pre-trained neural network for providing labels to anatomical landmarks of one or more medical input images of said subject at said one or more postures of said subject received from the input interface, and for providing one or more medical output images for subsequent clinical assessment of the spine of said subject which are input into the pre-trained neural network by a input interface;

wherein the pre-trained neural network has been pre-trained utilising or more medical training images corresponding to one or more predetermined postures of training subjects acquired from a plurality of training subjects at one or more predetermined postures wherein said one or more predetermined postures are postures utilized for clinical assessment of malalignment of the spine of said subject, and wherein the anatomical landmarks of the spine of said one or more medical training images acquired from the plurality of training subjects have been pre-labeled by a clinician; and wherein the one or more postures of said subject for which the one or more medical input images of the subject acquired correspond to one or more of said predetermined postures; and an output module for displaying the one or more medical output images of the spinal region of said subject having said labels provided thereto by the pre-trained neural network, for clinical assessment.

The medical image may be selected from the group including CT (computer tomography) scans, X-ray, MRI (magnetic resonance imaging, CBCT (Cone beam computed tomography) or the like.

In a sixth aspect, the present invention provides a computerized system for providing one or more images of the spinal region of a subject for which anatomical landmarks applicable for clinical assessment are labeled for clinical assessment of malalignment of a spine of a subject, the computerized system including:

an input interface for receiving one or more medical images of a subject, wherein each medical input image of the one or more medical input images is an image of said subject at one or more postures of said subject;

a pre-trained neural network for providing labels to anatomical landmarks of one or more medical input images of said subject at said one or more postures of said subject received from the input interface, and for providing one or more medical output images for subsequent clinical assessment of the spine of said subject which are input into the pre-trained neural network by a input interface;

wherein the pre-trained neural network has been pre-trained utilising or more medical training images corresponding to one or more predetermined postures of training subjects acquired from a plurality of training subjects at one or more predetermined postures wherein said one or more predetermined postures are postures utilized for clinical assessment of malalignment of the spine of said subject, and wherein the anatomical landmarks of the spine of said one or more medical training images acquired from the plurality of training subjects have been pre-labeled by a clinician; and wherein the one or more postures of said subject for which the one or more medical input images of the subject acquired correspond to one or more of said predetermined postures;

a processor module for processing the one or more medical input images of the spinal region of said subject having said labels provided thereto by the pre-trained neural network by way of one or more rules-based assessment criteria based on the labelled anatomical landmarks so as to provide assessment data; and an output module, for displaying said assessment data for clinical assessment.

The rules-based assessment criteria is preferably a clinical assessment criteria. The clinical assessment criteria may be Cobb angle assessment.

In a seventh aspect, the present invention provides a process operable using a computerized system for providing one or more output images of a region of interest of a subject for which anatomical landmarks applicable for clinical assessment are labeled in a pre-trained neural network for clinical assessment of malalignment of a the bone structure of a subject at said region of interest, the computerized system including an image data acquisition device, a pre-trained neural network and an output module operably interconnected together via a communication link, said process including the steps of:

(i) by an image data acquisition device, acquiring one or more data input sets indicative of the spinal region of a subject, wherein each data input set of the one or more data input sets is indicative of an optical image of said subject at one or more corresponding postures of the subject;

(ii) in a pre-trained neural network, providing labels to anatomical landmarks of said one or more data input sets each of which is indicative of said optical image of the subject at said one or more postures of the subject acquired during step (i) so as to provide one or more optical output images for subsequent clinical assessment of the region of interest of said subject, wherein the pre-trained neural network has been pre-trained utilising one or more training data input sets corresponding to one or more predetermined postures of training subjects acquired from a plurality of training subjects, wherein said one or more predetermined postures are postures utilized for clinical assessment of malalignment of the bone structure of a subject at said region of interest; wherein the anatomical landmarks of the bone structure of said one or more training data input sets acquired from said plurality of training subjects have been pre-labeled by at least one clinician; and wherein the one or more postures of said subject for which the one or more data input sets of the subject acquired during step (i) correspond to one or more of said predetermined postures; and (iii) displaying by the output module, the one or more optical output images of the spinal region of said subject having said labels provided thereto by the pre-trained neural network, for clinical assessment.

In an eighth aspect, the present invention provides a process operable using a computerized system for providing one or more output images of the region of interest of a subject for which anatomical landmarks applicable for clinical assessment are labeled for clinical assessment of malalignment of a bone structure of a subject, the computerized system including an input interface, a pre-trained neural network and an output module operably interconnected together via a communication link, said process including the steps of:

(i) acquiring one or more medical input images of a subject, wherein each medical input image of the one or more medical input images is an image of said subject at one or more corresponding postures;

(ii) in a pre-trained neural network, providing labels to anatomical landmarks of one or more medical input images of said subject at said one or more postures of the subject acquired during step (i) for providing one or more medical output images for subsequent clinical assessment of the region of interest of said subject which are input into a pre-trained neural network by a input interface;

wherein the pre-trained neural network has been pre-trained utilising or more medical training images corresponding to one or more predetermined postures of training subjects acquired from a plurality of training subjects at one or more predetermined postures;

wherein said one or more predetermined postures are postures utilized for clinical assessment of malalignment of the bone structure at the region of interest of said subject, and wherein the anatomical landmarks of the bone structure at the region of interest of said one or more medical training images acquired from the plurality of training subjects have been pre-labeled by at least one clinician; and wherein the one or more postures of said subject for which the one or more medical input images of the subject acquired during step (i) correspond to one or more of said predetermined postures; and (iii) displaying by the output module, the one or more medical output images of the spinal region of said subject having said labels provided thereto by the pre-trained neural network, for clinical assessment.

In a ninth aspect, the present invention provides process operable using a computerized system for providing one or more images of a region of interest of a subject for which anatomical landmarks applicable for clinical assessment are labeled for clinical assessment of malalignment of the bone structure at the region of interest of a subject, the computerized system including an input interface, a pre-trained neural network and an output module operably interconnected together via a communication link, said process including the steps of:

(i) acquiring one or more medical input images of a subject, wherein each medical input image of the one or more medical input images is an image of said subject at one or more postures of said subject;

(ii) in a pre-trained neural network, providing labels to anatomical landmarks of one or more medical input images of said subject at said one or more postures of the subject acquired during step (i) for subsequent clinical assessment of the region of interest of said subject which are input into a pre-trained neural network by a input interface;
  wherein the pre-trained neural network has been pre-trained utilising or more medical training images corresponding to one or more predetermined postures of training subjects acquired from a plurality of training subjects at one or more predetermined postures
  wherein said one or more predetermined postures are postures utilized for clinical assessment of malalignment of the bone structure at the region of interest of said subject, and wherein the anatomical landmarks of the bone structure at the region of interest of said one or more medical training images acquired from the plurality of training subjects have been pre-labeled by a clinician; and
  wherein the one or more postures of said subject for which the one or more medical input images of the subject acquired during step (i) correspond to one or more of said predetermined postures; and
(iii) in a processor module, processing the one or more medical input images of the spinal region of said subject having said labels provided thereto by the pre-trained neural network by way of one or more rules-based assessment criteria based on the labelled anatomical landmarks so as to provide assessment data; and
(iv) displaying by the output module, said assessment data from step (iii) for clinical assessment.

The region of interest may be the spinal region of a subject, the pelvic region of a subject, the femoral-pelvic region of a subject, or the leg region of a subject.

In a tenth aspect, the present invention provides a computerized system for providing one or more images of the spinal region of a subject for which anatomical landmarks applicable for clinical assessment are labeled for clinical assessment of malalignment of a region of interest of a subject, the computerized system including:
  an image data acquisition device, for acquiring one or more data input sets of the spinal region of a subject, wherein each data input set of the one or more data input sets is indicative of an optical image of said subject at one or more corresponding postures of the subject;
  a pre-trained neural network, for providing labels to anatomical landmarks of said one or more data input sets indicative of the subject at said one or more postures of the subject acquired from the image data acquisition device for providing optical output images for subsequent clinical assessment of the bone structure at the region of interest of said subject,
  wherein the pre-trained neural network has been pre-trained one or more training data input sets corresponding to one or more predetermined postures of training subjects acquired from a plurality of training subjects,
  wherein said one or more predetermined postures are postures utilized for clinical assessment of malalignment of the bone structure at the region of interest of a subject; wherein the anatomical landmarks of the bone structure at the region of interest of said one or more training data input sets acquired from said plurality of training subjects have been pre-labeled by at least one clinician and;
  wherein the one or more postures of said subject for which the one or more data input sets indicative of the subject is acquired correspond to one or more of said predetermined postures; and
  an output module, for displaying the one or more optical output images of the spinal region of said subject having said labels provided thereto by the pre-trained neural network, for clinical assessment.

In a eleventh aspect, the present invention provides a computerized system for providing one or more images of the spinal region of a subject for which anatomical landmarks applicable for clinical assessment are labeled for subsequent clinical assessment of malalignment of a bone structure at the region of interest of a subject, the computerized system including:
  an input interface for receiving one or more medical input images of a subject, wherein each medical input image of the one or more medical input images is an image of said subject at one or more corresponding postures,
  a pre-trained neural network for providing labels to anatomical landmarks of one or more medical input images of said subject at said one or more postures of said subject received from the input interface, and for providing one or more medical output images for subsequent clinical assessment of the bone structure at the region of interest of said subject which are input into the pre-trained neural network by a input interface;
  wherein the pre-trained neural network has been pre-trained utilising or more medical training images corresponding to one or more predetermined postures of training subjects acquired from a plurality of training subjects at one or more predetermined postures
  wherein said one or more predetermined postures are postures utilized for clinical assessment of malalignment of the bone structure at the region of interest of said subject, and wherein the anatomical landmarks of the bone structure at the region of interest of said one or more medical training images acquired from the plurality of training subjects have been pre-labeled by a clinician; and
  wherein the one or more postures of said subject for which the one or more medical input images of the subject acquired correspond to one or more of said predetermined postures; and
  an output module for displaying the one or more medical output images of the spinal region of said subject having said labels provided thereto by the pre-trained neural network, for clinical assessment.

In a twelfth aspect, the present invention provides computerized system for providing one or more images of the spinal region of a subject for which anatomical landmarks applicable for clinical assessment are labeled for clinical assessment of malalignment of a bone structure at the region of interest of a subject, the computerized system including:
  an input interface for receiving one or more medical images of a subject, wherein each medical input image of the one or more medical input images is an image of said subject at one or more postures of said subject;
  a pre-trained neural network for providing labels to anatomical landmarks of one or more medical input images of said subject at said one or more postures of said subject received from the input interface, and for providing one or more medical output images for subsequent clinical assessment of the bone structure at the region of interest of said subject which are input into the pre-trained neural network by a input interface;
  wherein the pre-trained neural network has been pre-trained utilising or more medical training images corresponding to one or more predetermined postures of training subjects acquired from a plurality of training subjects at one or more predetermined postures wherein said one or more predetermined postures are postures utilized for clinical assessment of malalignment of the bone structure at the region of interest of said subject, and wherein the anatomical landmarks of the bone structure at the region of interest of said one or more medical training images acquired from the plurality of training subjects have been pre-labeled by a clinician; and wherein the one or more postures of said subject for which the one or more medical input images of the subject acquired correspond to one or more of said predetermined postures;

a processor module for processing the one or more medical input images of the spinal region of said subject having said labels provided thereto by the pre-trained neural network by way of one or more rules-based assessment criteria based on the labelled anatomical landmarks so as to provide assessment data; and an output module, for displaying said assessment data for clinical assessment.

The region of interest may be the spinal region of a subject, the pelvic region of a subject, the femoral-pelvic region of a subject, or the leg region of a subject.

In a thirteenth aspect, the present invention provides a process operable using a computerized system for providing one or more output images of a region of interest of a subject for which anatomical landmarks applicable for clinical assessment are labeled in a pre-trained neural network for clinical assessment of malalignment of a the bone structure of a subject at said region of interest, the computerized system including an image data acquisition device, a pre-trained neural network and an output module operably interconnected together via a communication link, said process including the steps of:

(i) by an image data acquisition device, acquiring one or more data input sets indicative of the region of interest of a subject, wherein each data input set of the one or more data input sets is indicative of an optical image of said subject at one or more corresponding postures of the subject;

(ii) in a pre-trained neural network, providing labels to anatomical landmarks of said one or more data input sets each of which is indicative of said optical image of the subject at said one or more postures of the subject acquired during step (i) so as to provide one or more optical output images for subsequent clinical assessment of the region of interest of said subject, wherein the pre-trained neural network has been pre-trained utilising one or more training data input sets corresponding to one or more predetermined postures of training subjects acquired from a plurality of training subjects, wherein said one or more predetermined postures are postures utilized for clinical assessment of malalignment of the bone structure of a subject at said region of interest; wherein the anatomical landmarks of the bone structure of said one or more training data input sets acquired from said plurality of training subjects have been pre-labeled utilizing one or more rules-based criteria based on identification of anatomical landmarks of the bone structure of said one or more training data input sets; and wherein the one or more postures of said subject for which the one or more data input sets of the subject acquired during step (i) correspond to one or more of said predetermined postures; and (iii) displaying by the output module, the one or more optical output images of the region of interest of said subject having said labels provided thereto by the pre-trained neural network, for clinical assessment.

In a fourteenth aspect, the present invention provides a process operable using a computerized system for providing one or more simulated medical output images of a region of interest of a subject for which anatomical landmarks applicable for clinical assessment are labeled in a pre-trained neural network for clinical assessment of malalignment of a the bone structure of a subject at said region of interest, the computerized system including an image data acquisition device, a pre-trained neural network and an output module operably interconnected together via a communication link, said process including the steps of:

(i) by an image data acquisition device, acquiring one or more data input sets indicative of the region of interest of a subject, wherein each data input set of the one or more data input sets is indicative of an optical image of said subject at one or more corresponding postures of the subject;

(ii) in a pre-trained neural network, providing labels to anatomical landmarks to one or more simulated medical image, wherein said one or more medical image and said anatomical landmarks are generated based upon said one or more data input sets acquired during step (i), so as to provide one or more simulated medical images corresponding to the one or more acquired data input sets of the region of interest said subject, having said labels provided thereto by the pre-trained neural network;

wherein the pre-trained neural network has been pre-trained utilising one or more training data input sets and one or more medical images acquired simultaneously when the one or more data input sets are acquired from the plurality of training subjects, wherein said one or more training data input sets correspond to one or more predetermined postures of said training subjects acquired from a plurality of training subjects, and wherein anatomical landmarks of at least the one of said one or more training data input sets and said one or more medical images have been pre-labelled;

wherein said one or more predetermined postures are postures utilized for clinical assessment of malalignment of the bone structure of a subject at said region of interest; and wherein the one or more postures of said subject for which the one or more data input sets of the subject acquired during step (i) correspond to one or more of said predetermined postures; and (iii) displaying by the output module, the one or more simulated medical output images of the region of interest of said subject having said labels provided thereto by the pre-trained neural network, for clinical assessment.

The anatomical landmarks of the bone structure of said one or more training data input sets acquired from said plurality of training subjects have been pre-labeled.

The anatomical landmarks of the bone structure of said one or more medical images acquired from said plurality of training subjects may have been pre-labeled.

The anatomical landmarks of said one or more training data input sets and the bone structure of said one or more medical images acquired from said plurality of training subjects may have been pre-labeled.

The anatomical landmarks of the bone structure of said one or more training data input sets acquired from said plurality of training subjects have been pre-labeled utilizing one or more rules-based criteria based on identification of anatomical landmarks of the bone structure of said one or more training data input sets.

The region of interest may be the spinal region of a subject. the pelvic region of a subject, the femoral-pelvic region of a subject, or the leg region of a subject.

In a fifteenth aspect, the present a computerized system for providing one or more images of the region of interest of a subject for which anatomical landmarks applicable for clinical assessment are labeled for clinical assessment of malalignment of a region of interest of a subject, the computerized system including:

an image data acquisition device, for acquiring one or more data input sets of the region of interest of a subject, wherein each data input set of the one or more data input sets is indicative of an optical image of said subject at one or more corresponding postures of the subject;

a pre-trained neural network, for providing one or more simulated medical output images of the region of interest of said subject having labels provided thereto by the pre-trained neural network wherein the pre-trained neural network has been pre-trained utilising one or more training data input sets and one or more medical images acquired simultaneously when the one or more data input sets are acquired from the plurality of training subjects, wherein said one or more training data input sets correspond to one or more predetermined postures of said training subjects acquired from a plurality of training subjects, and wherein anatomical landmarks of at least the one of said one or more training data input sets and said one or more medical images have been pre-labelled;

wherein said one or more predetermined postures are postures utilized for clinical assessment of malalignment of the bone structure of a subject at said region of interest; and wherein the one or more postures of said subject for which the one or more data input sets of the subject acquired correspond to one or more of said predetermined postures; and an output module, for displaying the one or more simulated of the region of interest of said subject having said labels provided thereto by the pre-trained neural network, for clinical assessment.

In a sixteenth aspect, the present invention provides an image data acquisition device, for acquiring one or more data input sets of the region of interest of a subject, for which anatomical landmarks applicable for clinical assessment are labeled for clinical assessment of malalignment of a region of interest of the subject, wherein said device is used in a system for providing one or more images of the region of interest of a subject for which anatomical landmarks applicable for clinical assessment are labeled for clinical assessment of malalignment of a region of interest of a subject, the computerized system including:

an image data acquisition device, for acquiring one or more data input sets of the region of interest of a subject, wherein each data input set of the one or more data input sets is indicative of an optical image of said subject at one or more corresponding postures of the subject;

a pre-trained neural network, for providing one or more simulated medical output images of the region of interest of said subject having labels provided thereto by the pre-trained neural network wherein the pre-trained neural network has been pre-trained utilising one or more training data input sets and one or more medical images acquired simultaneously when the one or more data input sets are acquired from the plurality of training subjects, wherein said one or more training data input sets correspond to one or more predetermined postures of said training subjects acquired from a plurality of training subjects, and wherein anatomical landmarks of at least the one of said one or more training data input sets and said one or more medical images have been pre-labelled;

wherein said one or more predetermined postures are postures utilized for clinical assessment of malalignment of the bone structure of a subject at said region of interest; and wherein the one or more postures of said subject for which the one or more data input sets of the subject acquired correspond to one or more of said predetermined postures.

The device may include an output module, for displaying the one or more simulated of the region of interest of said subject having said labels provided thereto by the pre-trained neural network, for clinical assessment.

BRIEF DESCRIPTION OF THE DRAWINGS

In order that a more precise understanding of the above-recited invention can be obtained, a more particular description of the invention briefly described above will be rendered by reference to specific embodiments thereof that are illustrated in the appended drawings. The drawings presented herein may not be drawn to scale and any reference to dimensions in the drawings or the following description is specific to the embodiments disclosed.

FIG. 2a(i) depicts a flow chart showing an embodiment of a process to diagnose and track the development of the spinal alignment of a person with the use of the system as illustrated in FIG. 1a.

FIG. 2a(ii) depicts a flow chart showing another embodiment of a process to diagnose and track the development of the spinal alignment of a person with the use of the system as illustrated in FIG. 1a.

DETAILED DESCRIPTION OF THE DRAWINGS

Figure 1A:
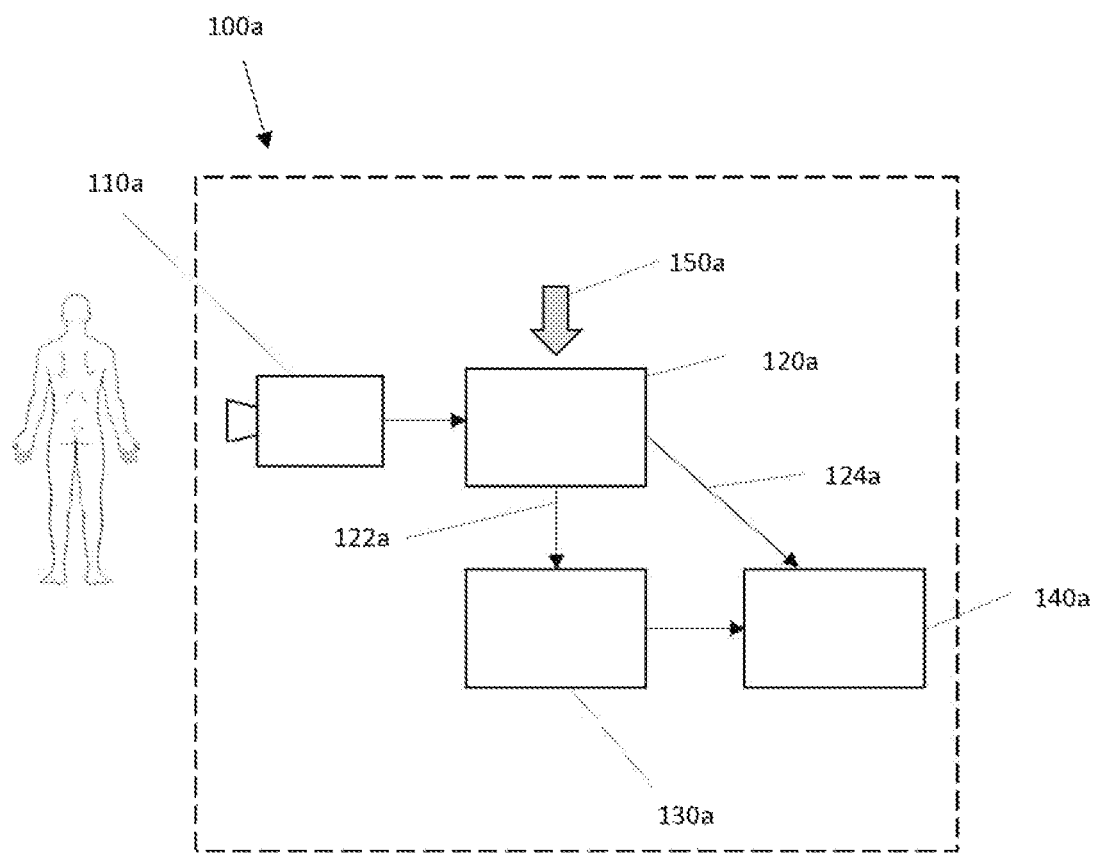
FIG. 1a shows a schematic representation of an embodiment of a system for diagnosing and tracking of the development of the spinal alignment of a person according to the present invention.

The present inventors have identified shortcomings of the problems with the prior art, and have provided a system which is more consistent and reliable, and overcomes the problems of the prior art.

Specific Background of the Invention

A human's spine is normally made up of 33 vertebrae stacking on top of each other, separated by discs for shock absorption during movement. It is the combination of these vertebrae which allows the spine to move in many different directions dynamically.

The vertebrae in the human vertebral column are divided into different regions, which correspond to the curves of the spinal column. These regions, from top to bottom, being the cervical spine, the thoracic spine, the lumbar spine, the sacrum and the coccyx.

As is known, a normal and healthy spine does not appear as an absolute straight column, it is rather defined as a natural S-shape when viewed from the side (sagittal view). This shape allows for an even distribution of weight and flexibility of movement for upright activities.

However, curvature at different regions of the spine can be excessive and exaggerated, leading to pain, deformity and neurologic dysfunction, cardiovascular and pulmonary disorders in extreme cases. Such abnormal curvature of a spine is often referred to as spinal malalignment.

A slight spinal malalignment can be asymptomatic and may not even be visible when a person is of a normal standing posture. However, when the abnormal curvature of the spine is too excessive that causes compression to the nerves, especially the spinal nerves and/or the cord, it may lead to stiffness, numbness or even serious pain in the neck, back and down to the limbs.

Spinal malalignment can be classified by its deformity pattern. Common spinal curvature disorders include Scoliosis, Kyphosis, Lordosis and Kyphoscoliosis, and among these, Scoliosis is one of the most common spinal disorder, occurring in 0.5% of the world population.

Scoliosis is a medical condition in which a person's spine has an abnormal lateral curvature, such that when viewed from the back, the spine of a patient appears as an "S" or "C" shape.

Usually such abnormal curve is mild and does not affect a person's appearance or health. Symptoms of a mild scoliosis may include uneven shoulders, uneven waistlines and uneven backs when bending forward.

However, when scoliosis progresses over time, it can also cause back pain, shortness of breath, restricted mobility, numbness in the limbs and in some serious cases, may even lead to bone and joint damages.

It is noticed clinically that most cases of scoliosis occur in adolescents aged between nine to fifteen years old, when the abnormal curvature of the spine becomes more noticeable. Scoliosis of young person during adolescence is often referred to as Adolescent Idiopathic Scoliosis (AIS).

AIS is so common that it could be found as many as 4 in 100 adolescents. In general, AIS curves progress during the rapid growth period of the patient. While most curves slow their progression significantly at the time of skeletal maturity, some, especially curves greater than 60 degrees, continue to progress during adulthood.

Prompt diagnosis of early-onset scoliosis is important for successful treatment of spinal curves and optimal long-term results for young adults. Since the abnormal progression of the spine is permanent, any untreated early onset scoliosis will likely lead to a much more profound negative impact on overall health of the young adult.

As such, it is often advisable for adolescents aged between nine to fifteen to have regular inspection on their spinal curvature, so as to make sure the spine is of healthy growth.

Examination on symmetry of the back by standing, raters shall from anterior, posterior and lateral aspects with appropriate exposure of the patient. Shoulder height, waist asymmetry, thoracic cavity asymmetry, rib, and breast deformity are recorded.

Adams forward bend test is common for scoliosis diagnosis, prior to further imaging diagnosis. During the test, patient with scoliosis may present a prominent line where the spine is. Further X-ray imaging is necessary to confirm the diagnosis of scoliosis.

During Adam's forward bend test when a patient is in a forward bending position, a scoliometer would be placed over the spine of the patient to measure the trunk asymmetry. A scoliosis patient usually has one side of the back higher than the other in a certain degree, and such degree is read by the scoliometer which serves as an initial evaluation for scoliosis.

Observations by the Inventor

Although using a Scoliometer for measurements is useful in providing initial evaluation for scoliosis, it has been noted that the assessment can be subject to errors since the scoliometer reading of a patient may differ due to his/her variation in postures.

Further, since this is a manual measurement carried out by trained practitioners such as medical doctors and surgeons, each practitioner may carry out the assessment procedures a bit differently to the others, and therefore providing variations to the scoliometer readings of the patient.

Current assessment tools for spine alignment include physical examination and medical imaging.

Physical examination is essential in diagnosing nerve compression. However, in such physical examination, it cannot detect specific underlying pathology. Thus medical imaging technology assessment is necessary.

Common medical imaging techniques include x-ray, computed tomography (CT) and magnetic resonance imaging (MRI). X-ray and CT images and data can be used to demonstrate spinal canal stenosis and spinal column malalignment due to a high x-ray absorption rate of the bone. Additionally, MRI produces a high-quality image set of soft tissues for tracking their enlargement, degeneration, and migration.

While the medical imaging production is objective, the interpretation of imaging data is relatively subjectivity and therefore can contribute to inter-rater variance.

Another significant downside is that the repetitive radiation exposure required in managing spine alignment, which can potentially increase the risk of cancer especial in young growing children.

Current diagnosis and follow-up assessments require intensive clinician experience and expertise. All decisions are based mainly on the curve appearance on x-rays.

As such, young children are required to have x-rays every 6 months to have close monitoring of the deformity and to provide timely interventions. This inherently increases the radiation exposure in growing children This also increases the anxiety of parents or carers who must wait for the half-yearly x-ray examinations before being updated on the progress of the disease or progress of treatment.

The external appearance of the back of a patient, often a child, varies and it is difficult for the human eye to discern which curve has deteriorated or how the curve has negatively affected the body posture.

Clinically, it has been noted by the present inventor, there exists a lack of a visual tools or methods to quantify body shape changes of the young growing patients, as it the case with children and adolescents.

This absence and deficiency are clinical practice as identified by the present inventor, and the need for such a tool or method, is considered pertinent for clinical evaluation and for ease and improvement of treatment planning and progression monitoring.

Such a tool and method as lacking in the prior art is identified by the present inventor as of importance to be implement, as it can assist the clinicians:

(i) increased consistency in diagnosis,
(ii) increased efficiency and accuracy in procedure (either surgical intervention of non-surgical intervention);
(iii) treatment and procedure planning;
(iv) monitor for treatment progression and outcomes;
(v) improve the patient's compliance to treatment by demonstrating longitudinal treatment improvement; and
(vi) Reduce the patients' and carers' anxiety about the patients' condition.

As all patents, including scoliosis patients, require regular checking and monitoring at the clinics and hospitals, a high everyday patient flow to these healthcare facilities is created, leading to huge workload of each practitioner and reduced consulting time for the patients. At the same time, it is highly time consuming and cost ineffective for patients to always schedule visits to the clinics or hospitals for regular checking.

Further, during either the standing test or the Adam's forward bend test, a patient is required to undress in order to expose the spinous process on the bare back to the practitioners for examination.

This could be highly uncomfortable to patients, especially adolescent patients, since no one would want to undress in unfamiliar environments and in front of or near to another person, Further, such children typically do not feel comfortable in having their backs touched by strangers.'

Disadvantageously, the rushed and uncomfortable environment of such assessment may result in less than optimal assessments, in addition to discomfort and inconvenience to both a child and a career to attend a clinical facility for such evaluation and follow-up.

Similar observations have been made by the present inventor, assessment of patents who may have degenerative malalignment (low back pain) patient cohort with degenerative scoliosis (abnormal cobb angle and trunk shift) or sagittal mal alignment (abnormal kyphotic angle, lumbar lordosis, pelvic incidence, pelvic tilt and/or sacral slope) face similar inconveniences and difficulties, and the present invention is useful not only to scoliosis patients but also apply for the whole spinal malalignment population including idiopathic and degenerative cohort.

The present inventor, collectively in view of their observations of the need for clinical consistency, ease of acquisition of data and reliability and consistency, and social impact on patients, particularly children and their careers, and in view of the above, therefore provided for a new process and system which seeks to address at least some of the deficiencies, and provide system and process which address or improves upon deficiencies as identified by the present inventor as associated with the prior art.

Present Invention Detailed Description

Referring to FIG. 1a which shows an embodiment of a system 100a according to the present invention for assessing the spinal alignment of a person, typically that of a child, based on acquired optical images of the back of the subject.

As shown in FIG. 1a, the assessment system 100a includes an image data acquisition device 110a.

When a patient is ready for a spinal assessment, the image data acquisition device 110a acquiring one or more data input sets indicative of the spinal region of a subject, which may be a plurality of optical images of both the posterior and sagittal aspects of the patient, which clearly show the periphery of the body and the spinal alignment. Such data input sets may be based upon current clinical assessment and evaluation techniques as may be known within the art and including those as discussed above.

In embodiments of the present invention, the image data acquisition device may be an optical image acquisition device, and wherein the data input sets are optical input images.

The optical image acquisition device 110a may be, for example, a fixed CCD/CMOS camera installed in clinics or hospitals in a room or environment in which the image is to be acquired.

Alternatively, the optically image acquisition device 110a may also be a built-in camera of a specially designed mobile device or even daily used mobile devices for example smartphones and tablets.

Alternatively, the image data acquisition device may be a depth sensor, such as a depth camera. Notably and advantageously, by using such a portable image data acquisition device, such as a camera the image acquisition aspect of evaluation or assessment of the spine need not necessarily to be completed in clinics or hospitals, but anywhere that the patient feels comfortable with.

This has significant advantages including as follows:
(i) for patients or subject who may live a long distance from a hospital, thus not requiring careers to travel and interruption of schedules for careers as well as days lost for schooling for children;
(ii) due to images being acquired in one's home or a more comfortable environment progression monitoring and assessment, there maybe more accurate image acquisition with time for re-take of images;
(iii) again, in view of a more relaxed environment, the abovementioned and identified social and personal anxiety related issues are obviated.

It should be noted and understood, in current clinical practices, images are not acquired of subjects in various stances for measurement for assessment, and previous acquired measurements cannot be readily verified or even re-assessed.

The optical images acquired by the image acquisition device 110a are preferably RGB coloured images.

Alternatively, the acquired optical images can also be in greyscale, as long as the body and spinal features shown in the optical images are clear enough for image analysis.

As mentioned, optical images of the bare back of the patient are acquired from both the posterior and sagittal aspects thereof, since optical images form either one aspect can only provide limited information regarding the body shape and the spinal alignment of the patient. By combining optical images from both the posterior and sagittal aspects, more image data can be gathered for a thorough analysis and diagnosis.

Patients with spinal malalignment usually have the body twisted laterally to either side of the body, along the frontal plane of the body. Therefore, by acquiring optical images from the posterior aspect of the patient, information regarding the periphery of the body, balance and the body symmetry of the patient can be obtained for further analysis and assessment.

More symptoms indicating spinal malalignment of the patient can be identified from the posterior images of one's back, these symptoms include:
(i) Lateral inclination of the pelvic floor;
(ii) Vertical displacement of the scapulae;
(iii) Curvature of the spine (Spinal process); and
(iv) Linearity of the spinous process.

Further, optical images of the sagittal aspect of the patient provides a different set of information relating to the spinal alignment. Symptoms that may be viewed from the sagittal aspect of the patient include:
(i) Frontal inclination of the pelvic floor;
(ii) Horizontal displacement of the scapulae; and
(iii) Frontal curvature of the spine;

Therefore, by combining data obtained from optical images of both the posterior and sagittal aspects of the patient, more data indicating spinal inclination on different anatomy planes can be readily collected, and a more thorough image analysis and spinal diagnosis can be carried out.

The acquired optical images of the back of the patient are then input to a first neural network 120a which has been pre-trained, for image analysis and vertebral landmarks detection using artificial intelligence.

The pre-trained neural networks may be trained with "big data (a few thousands of images) utilising feature exaction" and/or with "small data (a few hundreds of images) utilising key point detection".

The neural network 120a further can, in embodiments of the invention, be comprises of two different components, including the Convolutional Neural Networks (CNNs) and the Recurrent Neural Network (RNN).

In an embodiment of the present invention, for malalignment assessment and X-ray simulation based on the optical images, a Convolutional Neural Networks (CNNs) based framework is utilised to extract images features and process regression, in order to evaluate the spine alignment of the patients. Specially designed Normalisation and Correction Algorithms may be applied so as to standardise input images, and reduce errors from different image qualities.

Image augmentation algorithms may also be also applied to enhance the robustness and accuracy of our proposed framework. Batch Normalization and Residual Blocks are applied in CNNs Model to obtain an improved configuration of the network.

In order to estimate the disease progression in embodiments of the invention, a Recurrent Neural Network (RNN) based model may be used to estimate malalignment progression in time series using an electronic Health Record, with Principle Component Analysis for feature selection.

Several indexes may be used for model training including medical images, sex, age, height, weight, alignment measurements with follow-ups with Long Short-term Machine (LSTM) to estimate the progression.

Mean Square Error (MSE) is used as a loss function and Back-propagation through time (BPTT) is chosen for model optimisation. The prognostic of future scoliosis curve behaviour, for example, is estimated in a timeframe of 3-month, 6-month, and 1-year.

It must be noted that the neural network 120a is required to be trained, such that upon a sufficient amount of input data before it can automatically locate the essential vertebral landmarks on the optical image of the back of a patient or subject.

Again, the pre-trained neural networks may be trained with "big data (a few thousands of images) utilising feature exaction" and/or with "small data (a few hundreds of images) utilising key point detection".

Preferably, the neural network 120a is to be trained with preferably at least 1000 sets of data before its results become accurate.

In order to train the neural network 120a, medical specialists, typically doctors, spinal surgeons or trained personnel in the field of orthopaedics or rehabilitation, are required to manually label and mark the locations of the essential vertebral landmarks on the acquired optical images of the posterior and sagittal aspect of a plurality of patients.

The manual labelling of raw optical images performed by trained practitioners can simply be achieved by applying dots and lines to the essential features or prominences of the spine as are shown and can be seen on the acquired optical images. Clinically useful and appropriate vertebral landmarks that are required to be manually labelled may include:
C7: Vertebra prominins
T3: At the level of the line connecting the two scapular spines
T7: At the level of the line connecting the inferior angles of both scapulae
T12: Just below the twelfth ($12^{th}$) rib
L4: At the level of the line connecting the summits of the iliac crests
S2: At the level of the line connecting the posterior superior iliac spines Upon the completion of the manual labelling process, the acquired optical images of the back of the patients, together with the labelled images 150a, are both input to the neural network 120a for training via a machine learning process, which may include but not limited to deep learning or meta learning.

Still referring to FIG. 1a, the neural network 120a is in communication with the optical image acquisition device 110a, that upon acquisition of optical images of the back and side of the patients, the images will be sent to a well-trained neural network 120a for vertebral landmarks detection and identification.

Based on implemented computer based artificial intelligence, an unassessed input optical image will be automatically marked with essential landmarks thereon which are identified and located by the neural network 120a, without the assistance of any trained practitioners. This feature will assist the clinicians and patients to assess the external appearance more objectively.

In an embodiment, paired X ray images taken simultaneously with the optical images at the same posture of a subject may be used to train the neural network.

Thus, in such an embodiment, simulated X rays may be produced as the output of the neural network 120a when new optical images of a subject are acquired by the optical image acquisition device (110a) which are subsequently inputted into the neural network 120a.

Simulated X rays which are output from the neural network 120a are then sent to the processing module 130a as denoted by arrow 122a, which is in communication with the neural network 120a. The processing module 130a provides for image analysis and calculations to the labelled images and provides analysis results in relate to the spinal malalignment of the patient.

One of the image analysing calculations performed by the processing module 130a may be the Cobb angle measurement, which shows the spinal malalignment level of a patient, and based on which the trained practitioners would decide what type of treatment the patient requires.

Cobb angle is typically measured by the angle between the upper endplate of the upper most tilted (end) vertebrae and the lower endplate of the lower most tilted (end) vertebrae; Lumbar lordosis is measured by the angle upper endplate of L1 and upper endplate of S1; sacral slope is measured between the tangent line to the superior endplate of S1 and the horizontal plane; pelvic tilt is the angle between a line drawn from the midpoint of the centre of the femoral heads to the centre of the superior endplate of the sacrum and the vertical plane; pelvic incidence is defined as the angle between the line perpendicular to the sacral plate at its midpoint and the line connecting this point to the midpoint of the centre of the femoral heads.

Upon data processing within the processing module 130a, medical results such as the lateral inclination angle of the spine and the value of the Cobb angle will be output to the output module 140a for doctor's medical decisions and evaluation.

In another embodiment, the processing module 130a does not provide any diagnosis and may not necessarily be present, as represented in FIG. 1a by arrow 124a. In such an embodiment, the system 100a is used as a screening type system to determine, whether by a human or by the processor, if:
- the patient requires no further assessment, or
- whether further clinical examination/evaluation may be required, such as by medical imaging. The output module 140a may be a fixed monitor display installed at hospitals or clinics for displaying the image analysis results to the doctors for their medical decision.

The output module 140a can also be used demonstrating to the patient the optical images of his/her back, such that the patient can have a rough idea of how the spinal malalignment impacts upon him/her.

Further, by keeping a record of all the optical images of the patients throughout the treatment process, it can be utilised by both the patient and the medical doctor for progress tracking of the spinal malalignment, as to whether the malalignment has worsened, or improved upon appropriate treatment.

In embodiments of the invention, a specially designed mobile device, or mobile devices which are already owned by the patient, including the smartphone or tablet, wherein the image tracking of the patient's spinal development can be tracked via accessing to the mobile application installed therein.

In such a case, the specially designed mobile device or mobile device may include the optical image acquisition device 110a and the output module 140a, in a unitary device which may be portable and usable by a patient's carer or parent, or by a clinician, depending upon the implementation.

Figure 1B:
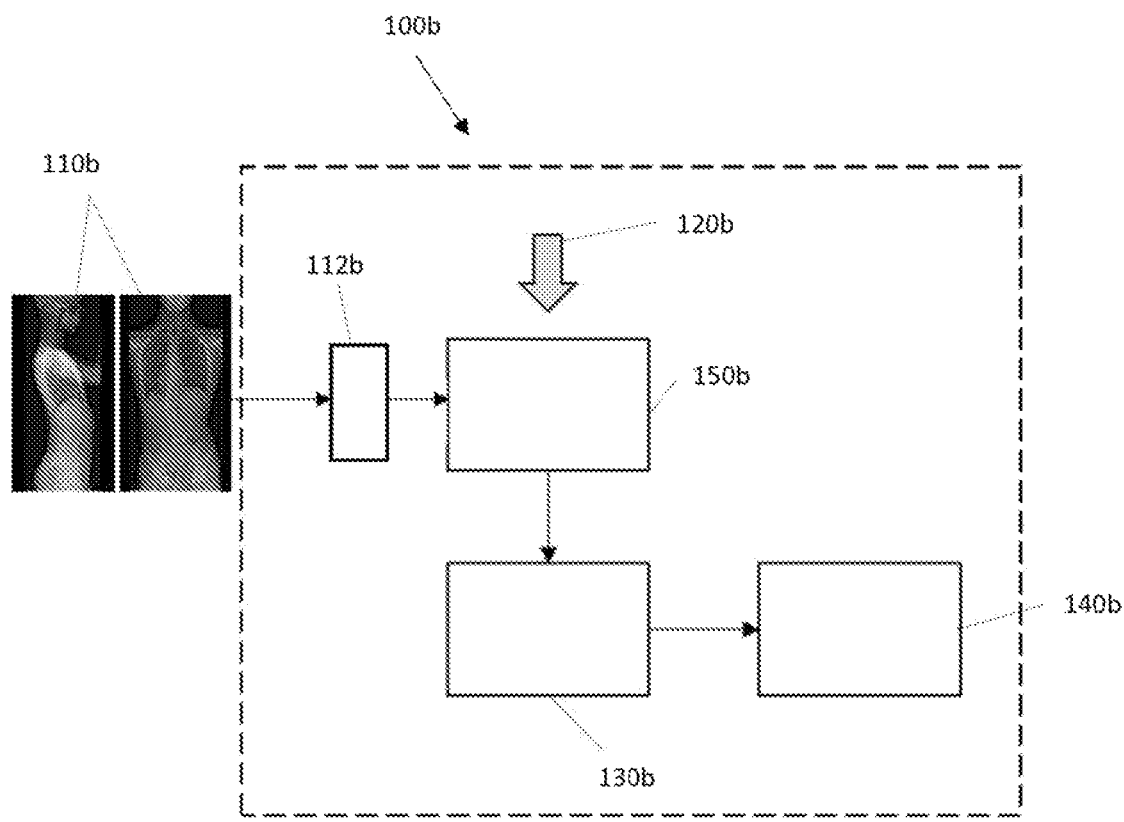
FIG. 1b shows a schematic representation of a further embodiment of a system for diagnosing and tracking of the development of the spinal alignment of a person according to the present invention.

Referring now to FIG. 1b, which shows a system 100b which is designed for diagnosing and tracking of the development of the spinal alignment of a patient, based on the acquired medical images of the back of a patient. These medical images may include CT scans, X-ray, MRI, CBCT (Cone beam computed tomography) or the like.

Similar to system 100a as described in FIG. 1a, medical images 110b of both the posterior and sagittal aspects of the patient which clearly show the spinous process of the patients are input to the system 100b.

The medical images for spinal assessments are input to a second neural network 120b of the system 100b for automatic landmarks detection via artificial intelligence.

Again, the second neural network 120b should be sufficiently trained before use. Trained practitioners including medical doctors and spinal surgeons are required to identify and manually label the essential vertebral landmarks on the medical images of a plurality of patients.

The raw medical images, together with the medical images which are manually labelled by the trained specialists 150b are then input by input interface 112b into the second neural network 120b for training via using machine learning methods, which includes but not limited to deep learning or and meta learning.

Upon sufficient training, the second neural network 120b is also appropriate to automatically identify and locate the essential and relevant vertebral or bone landmarks of any input medical images.

The labelled medical images output by the second neural network 120b is then sent to the processing module 130b for further analysis via rule-based assessments.

Taking scoliosis as an example, a novel Scoliosis Risk Assessment (SRA) Model may be built and implemented in realisation of the present invention.

To assess the model, the standardised application acquired patient images are tested in association with assigned ground-truth. Ground-truth labels are measured included Cobb Angel (CA) and/or Lumbar Lordosis angle (LL) from X-ray images by radiologists.

For pre-processing, the input images are treated by Intensity Normalization and Data Augmentation. Min-max normalisation is used to process data images in each channel for improved learning ability, it keeps original data distribution but puts pixel intensity values into a common range from '0' to '1'. Each Image is resized to 512×512×3 dimension with the colour channel being RGB format for example. Single grey-scale or GBR channel images can be converted to RGB format.

The maximum value of CA and LL are set as 90 degree within the application, and minimum value as 0 degree to include the severe cases with respiratory complication. For those are greater than 90 degree (rare condition), which is considered it as 90 degree for computational efficiency. Max-min normalization is applied to process CA and LL data, the range of value is between '0' to '1', with 0 degree converting to '0' and 90 degrees converting to '1'. The degrees between 0 to 90 are accordingly normalise between '0' to '1'.

Data Augmentation algorithms may be used to enhance the robustness of Convolutional Neural Networks (CNNs) and improve data information, to minimise the inaccurate model training caused by vary photographic techniques and devices. Input images are processed according to different spatial resolution, angle, brightness, contrast, position by data augmentation algorithms, and different Noise (e.g. Gaussian Noise), is added into images to simulate the hand-shaking effect during image capture.

Figure 2A:
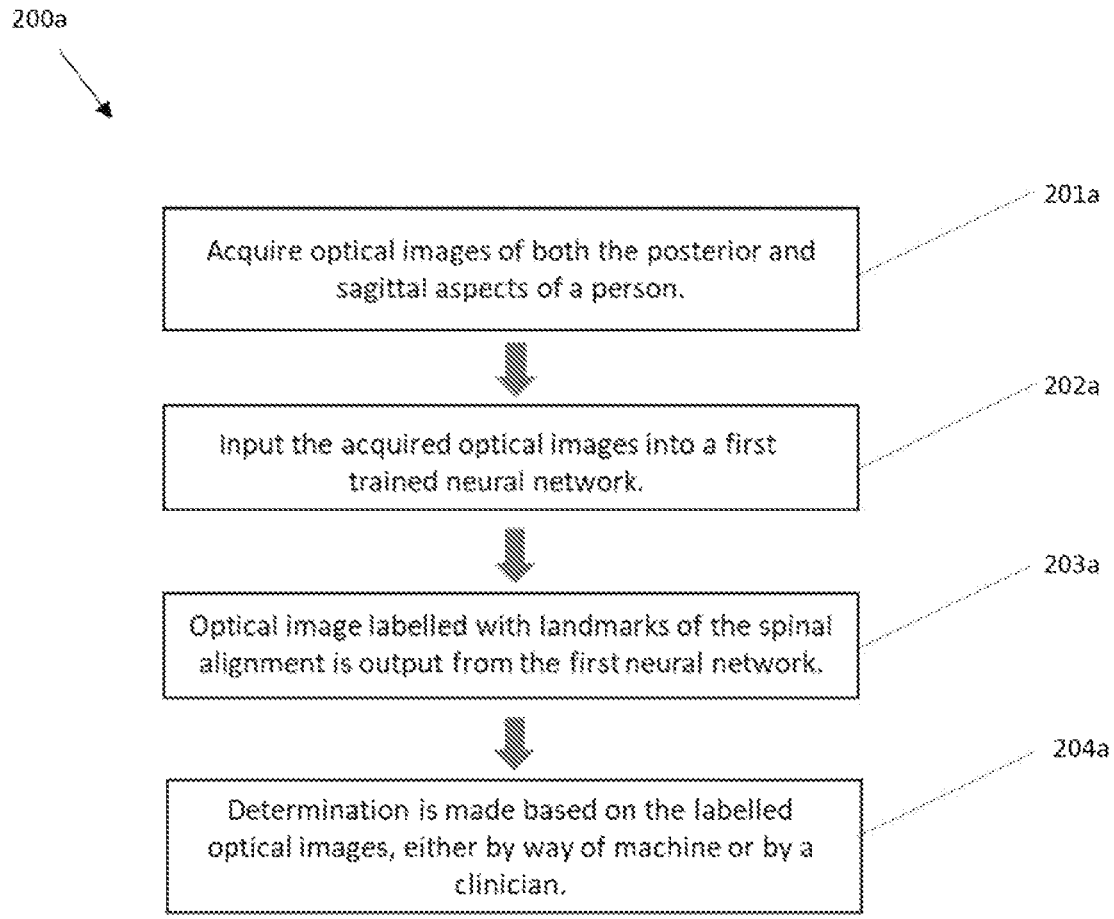

Referring to FIG. 2a(i), an embodiment of a process 200a in accordance with the present invention is shown, for the use of the first neural network is shown, wherein optical images such as is described with reference to FIG. 1a, of the posterior and sagittal aspects of the patient is required as an input.

Steps of the process 200a include:
(i) Acquire optical images of both the posterior and sagittal aspects of a person (201a);
(ii) Input the acquired optical images into a first trained neural network (202a);

(iii) Optical images labelled with landmarks of the spinal alignment is output from the first neural network (203a); and
(iv) Then a determination is made, either by way of machine or by a clinician (204a), if:
the patient requires no further assessment, or
whether further clinical examination/evaluation may be required, such as by medical imaging.

Output from the neural network may also be used for tracking for disease progression or treatment progression.

Referring to FIG. 2a(ii), an embodiment of a process 200aa in accordance with the present invention is shown, for the use of the first neural network is shown, wherein optical images such as is described with reference to FIG. 1a.

In the present embodiment, paired X ray images are acquired simultaneously with the corresponding optical images at the same posture of a subject may be used to train the neural network as described with reference to FIG. 1a above, and for subsequent provision of a simulated X ray based only on an input photographic image of a patient's body, which allows for the generation of a simulated and optionally labelled X ray for subsequent clinical assessment Steps of the process 200aa include:
(i) Acquire optical images of both the posterior and sagittal aspects of a person (201aa);
(ii) Input the acquired optical images into a first trained neural network (202aa);
(iii) Simulated X ray images based upon the acquired optical images are optionally labelled with landmarks and output from the neural network (203aa); and
(iv) Then a determination is made, either by way of machine or by a clinician (204aa) from the output, if:
the patient requires no further assessment,
whether further clinical examination/evaluation may be required, such as by medical imaging, or
any existing or previously identified ort diagnosed malalignment has been corrected effectively, or if ongoing treatment or therapy is required.

Output from the neural network may also be used for tracking for disease progression or treatment progression.

Thus, in such an embodiment, simulated X rays may be produced as the output of the neural network 120a when new optical images of a subject are acquired by the optical image acquisition device (110a) which are subsequently inputted into the neural network 120a.

Figure 2B:
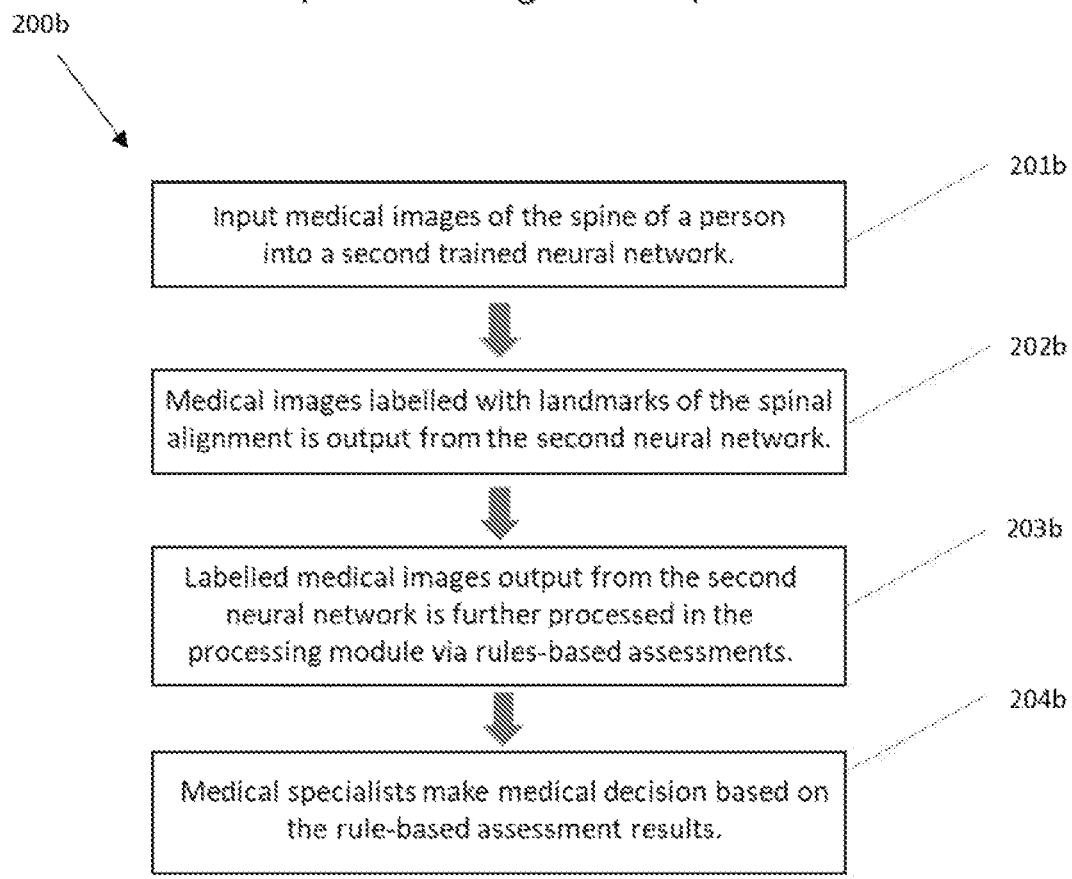
FIG. 2b refers to a flow chart showing a process to diagnose and track the development of the spinal alignment of a person with the use of the system as illustrated in FIG. 1b.

Simulated X rays which are output from the neural network 120a are then sent to the processing module 130a as denoted by arrow 122a, which is in communication with the neural network 120a. The processing module 130a provides for image analysis and calculations to the labelled images and provides analysis results in relate to the spinal malalignment of the patient. Similarly, FIG. 2b shows an embodiment of a process 200b of the present invention, using a second neural network, based on the input of medical images.

Steps of the process 200b include:
(i) Input medical images of the spine of a person into a second trained neural network (201b);
(ii) Medical images labelled with landmarks of the spinal alignment is output from the second neural network (202b);
(iii) Labelled medical images output from the second neural network is further processed in the processing module via rules-based assessments (203b); and
(iv) Medical specialists make medical decision based on the rule-based assessment results.

Figure 3:
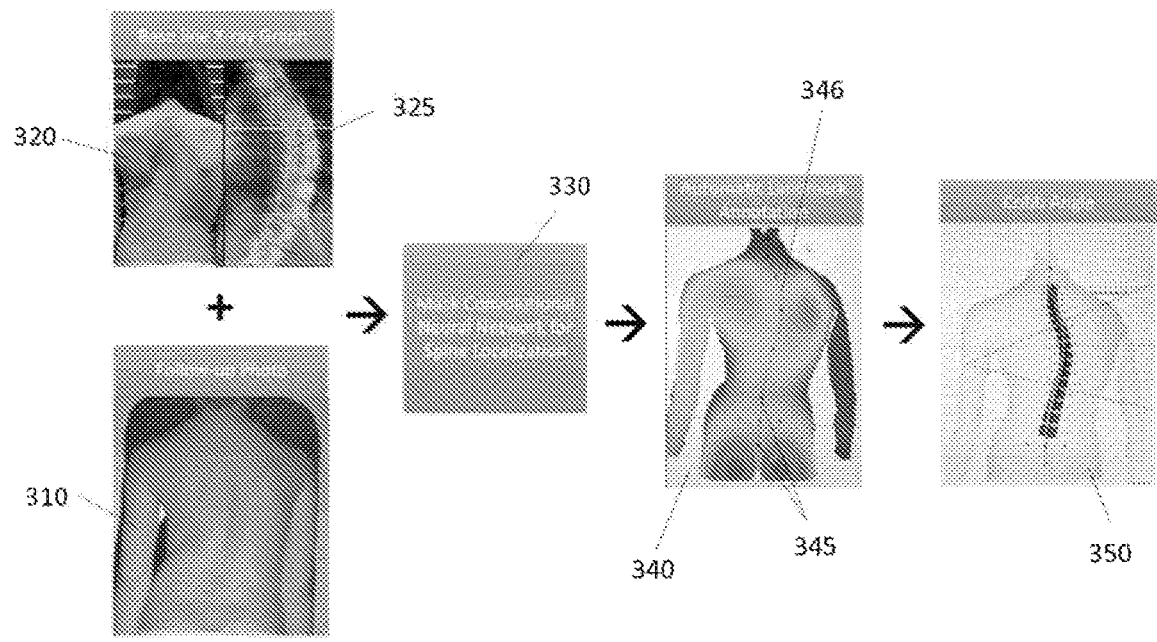
FIG. 3 illustrates a process for diagnosing and tracking the spinal malalignment according to the present invention.

Referring now to FIG. 3, there is shown a flowchart which illustrates a process 300 for diagnosing the spinal malalignment according to the present invention.

As mentioned in reference to FIGS. 1a and 1b, the system 100a and 100b include a neural network 120a and 120b for automatic detection of any essential vertebral landmarks on the input optical or medical images of the spine of the patient, such that it does not require assistance from trained practitioners including medical doctors and spinal surgeons to manually label the vertebral landmarks on the images for each patient.

As will be understood, the neural network needs to be well trained before use. As is shown in FIG. 3, the neural network 330 is trained upon a plurality of labelled optical images 320 and labelled medical images 325, essential vertebral landmarks therein are all manually identified and marked by trained practitioners.

After sufficient training via machine learning, for example but not limited to deep learning or meta learning, the neural network 330 is then ready for use for automatic landmarks detection of any input images.

During a spinal assessment according to an embodiment of the present invention, an optical image 310 of the posterior aspect of the patient is acquired, with the spinous process of the patient shown clearly in the image. The acquired image 310 is then input to the trained neural network 330 for automatic landmarks detection.

After processing within the neural network 330, a labelled image 340 with all essential vertebral landmarks marked and located is output. As is shown in the labelled image 340, the plurality of dots 345 indicates the essential landmarks which are automatically detected and marked by the neural network 330 based on artificial intelligence.

Still referring to the labelled image 340, by connecting all dots 345 which symbolises the essential vertebral landmarks together, a curve line 346 is formed which simulates the actual spinous process of the patient. The simulated spinous process of the patient may be useful for further calculations and analysis.

The labelled image 340 is then sent to the processing module, for further image analysis and calculations, by rules-based assessment criteria such as the clinical assessment criteria of Cobb angle assessment, for example calculating the Cobb Angle of the patient based on the labelled image 340. This can be shown in image 350, wherein the Cobb Angel is calculated by measuring the angle between the landmark of the upper endplate of the upper most tilted vertebrae and the landmark lower endplate of the lower most tilted vertebrae.

The calculated Cobb Angle value can be output to trained practitioners for their decision of what type of treatment is necessary for the patient.

The Cobb angle is a measure of the curvature of the spine in degrees. This provides assistance in assessment of malalignment of the spine, and also determine what type of treatment is necessary. Generally, a Cobb angle of 10 degree is regarded as a minimum angulation to define Scoliosis.

As will be understood by those skilled in the art, other rules-based assessment criteria for clinical application and assessment are equally applicable to the present invention.

Figure 4:
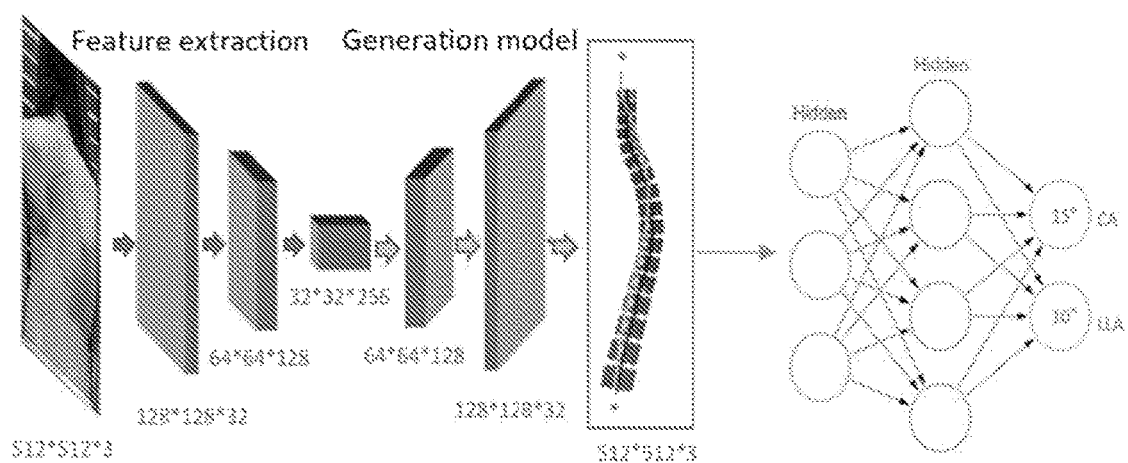
FIG. 4 shows the working mechanism of the neural networks within the diagnosis system according to the present invention.

Referring to FIG. 4 which shows a schematic representation of the neural network design 400.

As is shown, a deep learning-based model utilising CNNs for the present application is illustrated, which have two major functions: feature extraction and feature regression.

Firstly, Deep Residual Network is used for feature extraction, because Residual Learning can increase the depth of representation, which increases accuracy and efficiency in visual recognition tasks.

Furthermore, Max Pooling Layer is proposed to avoid over-fitting phenomenon, and batch Normalisation to reduce shifting of hidden unit values.

In model training process, for example, 70% of images are used for training and 10% for cross validation. Adam Optimization Algorithm is used for training weights and bias, which has function to avoid local minimization, with Mean Square Error for Loss Function. The remained data is for model test process, and the estimation accuracy can be improved by comparing the ground truth value and estimate value via SRA model.

Figure 5:
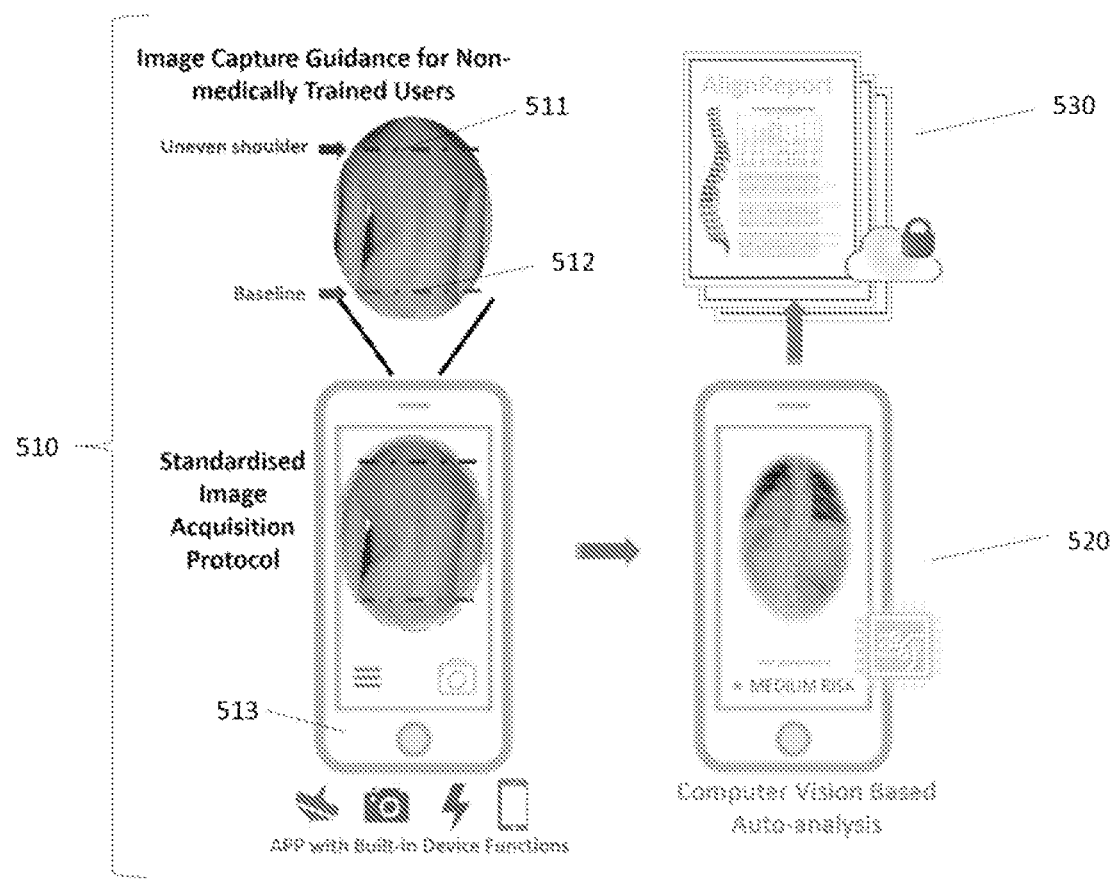
FIG. 5 shows a flow chart illustrating a process of using a mobile application installed in a smartphone for carrying out spinal assessment according to the present invention.

Referring to FIG. 5 which shows a flow chart illustrating the process 500 of using a mobile application installed in a smartphone 513 for carrying out spinal assessment according to the present invention.

As is shown in the first step 510 in FIG. 5, the built-in camera of the smartphone 513 is utilised as an optical image acquisition device to acquire optical images 515 of the back of the patient, either in posterior or sagittal aspect.

This allows the image acquisition process to possibly be carried out anywhere where the patient feels comfortable with, but not necessarily in clinics or hospitals, and fulfils identified deficiencies associated with the prior art as discussed above.

The image acquisition device may be a bespoke and purpose built item for image acquisition, and may also include a visual display unit for home monitoring and/or practitioner use.

This is beneficial to patients, especially adolescent patients, who would easily feel uncomfortable for undressing in unfamiliar environments, in front of unknown practitioners. By using the smartphone 513 as the optical image acquisition device, careers of the adolescent patients can easily acquire images at familiar environment such as the patient's bedroom or the school clinic, and therefore reduce any discomfort brought to the patients during spinal assessments.

In order to provide guidance to the careers who are not medically trained to correctly acquire suitable optical images for spinal assessment, reference lines 511 and 512 are provided in the mobile application such that when taking a photograph with the smartphone, the shoulders of the patient should align with the reference line 511, and that the pelvis of the patient should align with the reference line 512.

Upon acquisition of the optical images of the back of the patient, the process 500 enters to the second step 520 wherein the optical images of the patient are sent to a remote trained neural network for automatic landmarks detection, and a processing module for further image analysis via wireless communication for example Bluetooth or wifi. After which, calculations and analysis results will be output by the processing module.

As is shown in third step 530, calculations and analysis results output by the processing module is sent back to the smartphone type device via wireless communication for example Bluetooth or wifi, from the remote neural network and processing module.

The information is then output to the users via the smartphone 513, as to whether the patient is required to go back to the clinic for close monitoring, and also for the patient's own progress tracking.

Electronic Health Record Dataset

Electronic Health Record (eHR) of individuals acquired longitudinally through the present mobile application, can be used for disease progression estimation using Recurrent Neural Networks (RNNs). eHR contains information (including longitudinally collected X-ray images, sex, age, height, weight, follow-up Cobb Angles (CA) and/or Lumbar Lordosis Angles (LL)) that can be used to extract spine malalignment associated risk factors.

Various features of a disease can be automatically extracted by Recurrent Neural Networks (RNNs), which is a family of Neural Networks for classification with clustering and dimensional reduction based on sequential data. RNNs parameter sharing enables sequential data processing, thus the model can be trained to identify and learn vary features longitudinally with follow-ups. The output from processing previous records can be put back into the hidden layer, and information from previous records can influence the entire model. Therefore, the alignment parameters of patients in the follow-ups period can be estimated.

Data Processing

Through eHR database, many features can be achieved from patients. Principle Component Analysis (PCA) can be used for dimensional reduction to remove the useless and redundancy information for better efficiency. Features including Age of patients, sex/gender of patients are normalized between '0' to '1' for better learning ability. As described previously, max-min normalization is used to process alignment parameters data, the range of value is between '0' to '1', with data augmentation enhancing the robustness of RNN models.

RNNs Framework Design

Long Short-term Machine (LSTM) is adapted as Disease Progression Estimation Model), which is a specific Recurrent Neural Networks used to prevent vanishing gradient problem. Residual Learning Framework (ResNet) is used in this model to add skip connections through time, because deeper neural network can provide better performance for model training. Back-propagation through time (BPTT) optimises the model, and Mean Square Error (MSE) is chosen as loss function. Fast-RNN can used for this time-consuming work to reduce the running time of RNN model, exposing region proposal computation as a bottleneck.

Such rule-based results will be output to the output module 140 for medical specialists to make medical decision for the patients.

It will be noted and understood that although the invention is particularly described in reference to clinical assessment of scoliosis, the present invention is also useful for use in relation patients for the whole spinal malalignment population including idiopathic and degenerative cohort, and no limitation in this regard is implied.

Invention Advantages

The present invention provides numerous advantages and benefits within the field medical management and diagnostics, recovery, rehabilitation, screening and therapy for patients.

The present invention, in a broad form, provides a system and process which can provide an output image which can be used for clinical assessment or diagnosis of a subject select in respect of bone malalignment in a region of interest of the subject.

The region of interest of the subject may be any part of the skeletal system of the body of a subject, for example the spinal region of a subject including the neck thoracic and lumbar portions of the spine, the spinal region in the vicinity of the pelvis of the subject, the pelvic region of the subject, the femoral pelvic region of a subject and the leg portion or region of the subject.

As is known and as will be understood by those skilled in the art, in the event of malalignment or misalignment of bone or the skeletal structures within the body of a patient, often rehabilitation, follow up, further imaging and monitoring is required, in particular for management and maintenance and therapy in respect of deformities such as in the spinal region including scoliosis for example.

As will also be known by those skilled in the art, for such routine follow-up, it is inconvenient for a subject, in particular a child or adolescence common as well as the elderly, to travel to a clinic for follow up examination and diagnosis on a regular basis. It also can be quite traumatic for younger children and older children as well as adults to attend clinics for such routine follow up including X Ray, and physical examination which, due to the nature of such examination come up often requires the removal of the clothing or garments of a subject, which can cause embarrassment and feeling of vulnerability in some cases.

Also, in certain areas, it is inconvenient to regularly attend a clinic in a city or regional centres, and also inconvenient for children to miss extended times of schooling for example, to attend a clinic at a distance or even locally for follow up and assessment and routine examination.

The present invention, in embodiments thereof, overcomes or at least reduces such inconveniences by providing a process and a system which allows an image of a region of interest of a subject's body to be acquired by way of an optical or distance or death type acquisition device which acquires data indicative of an image or contours of the body of a subject.

As is known, in particular for routine follow up and for assessment of therapeutic effect and rehabilitation, bony prominences on the body of a subject, for example in the scapular region and the spinal region, are often used for the assessment of inclination, torsion deformation and malalignment of the spinal portion of a subject as well as the pelvis and femoral pelvic regions.

As provided by the present convention, an image can be conveniently acquired at home or in a clinic without the necessity to attend a hospital or large clinic, and the trauma associated therewith, by way of a portable acquisition device such as a digital camera or a depth measurement device. This may be a purpose-built device.

Several images may be acquired at different postures which are considered standard for assessment of bone alignment, for example scoliosis, and can provide an image which, may be processed in accordance with the present invention, and have their applied landmarks for the subsequent assessment by a clinician, or by application of a rules based assessment system on known such systems such as Cobb angle assessment, for determining and assessing the degree of malalignment of the spine.

Embodiments and aspects of the present invention are particularly convenient as it obviates the necessity for children in particular to attend a clinic and to line up with other children or other patients and wait for a clinical assessment by a stranger which due to the nature of such examinations can be uncomfortable, disconcerting common embarrassing, as well as provide anxiety to a child or adolescent who may be being assessed by a stranger, as well as cause concern or potential concern to parents or guardians of such children.

A depth sensor or camera has been found useful for detecting bony prominences in a subject and applicable to the present invention, as it typically is operable independent of ambient or surrounding light, and does not take false readings do too obstruction by shadow giving incorrect placement of bony prominences off the body of the subject.

Also, thermal imaging type image acquisition devices are also applicable to the present invention, and provide for acquisition of data indicative of and input image.

The present invention allows for ease of screening as well in an environment, for example remote from a large clinic, as by way of acquisition of an image of the external portion of the body of a subject in a region of interest, can be screened for the presence of deformity within or outside of a particular threshold of variation such as in assessment of spinal malalignment in scoliosis and utilization of assessment criteria such as cold angle or other such clinical assessment criteria or rules based assessment regimes.

By utilizing a trained neural network, the present invention allows for a high degree of accuracy which, as will be appreciated, is critical and important in the assessment of subjects from a clinical or therapeutic standpoint The trained neural network, in embodiments of the invention, can provide a simulated medical image, such as an X Ray typically, or a simulated MRI or other medical image, which can have anatomical landmarks labelled by the neural network for the subsequent assessment or screening by a clinician or other suitably experienced or qualified person.

The training of the neural network may be done utilising assessment by clinicians for example one or more clinicians, all by a rule spaced assessment and learning system, whereby anatomical landmarks are detected by the neural network and apply a rules based identification of Bony prominences for the marking of applicable anatomical landmarks for the subsequent assessment.

In embodiments of the invention, the neural network may be trained by the input of corresponding optical and medical image images of a subject at various postures applicable for assessment, and whereby the labels may be applied to either the optical image, the medical image or both for training of the neural network.

As will be understood by those skilled in the heart, the present invention has numerous applications for the assessment screening and determination of appropriate therapeutic therapy regimes including for rehabilitation and correction of malalignment of bone structures of a subject.

REFERENCES

[1] F. Schwab, A. Dubey, L. Gamez, A. B. El Fegoun, K. Hwang, M. Pagala, and J. P. Farcy, "Adult scoliosis: prevalence, SF-36, and nutritional parameters in an elderly volunteer population," Spine (Phila Pa 1976), vol. 30, no. 9, pp. 1082-5, May 1, 2005.

[2] F. Schwab, A. Dubey, M. Pagala, L. Gamez, and J. P. Farcy, "Adult scoliosis: a health assessment analysis by SF-36," Spine (Phila Pa 1976), vol. 28, no. 6, pp. 602-6, Mar. 15, 2003.

[3] F. J. Schwab, V. Lafage, J. P. Farcy, K. H. Bridwell, S. Glassman, and M. R. Shainline, "Predicting outcome and complications in the surgical treatment of adult scoliosis," Spine (Phila Pa 1976), vol. 33, no. 20, pp. 2243-7, Sep. 15, 2008.

[4] G. B. D. Disease, I. Injury, and C. Prevalence, "Global, regional, and national incidence, prevalence, and years lived with disability for 310 diseases and injuries, 1990-2015: a systematic analysis for the Global Burden of Disease Study 2015," Lancet, vol. 388, no. 10053, pp. 1545-1602, Oct. 8, 2016.

[5] T. Jackson, S. Thomas, V. Stabile, M. Shotwell, X. Han, and K. McQueen, "A Systematic Review and Meta-Analysis of the Global Burden of Chronic Pain Without Clear Etiology in Low- and Middle-Income Countries: Trends in Heterogeneous Data and a Proposal for New Assessment Methods," Anesth Analg, vol. 123, no. 3, pp. 739-48, September, 2016.

[6] E. Ferrero, B. Liabaud, V. Challier, R. Lafage, B. G. Diebo, S. Vira, S. Liu, J. M. Vital, B. Ilharreborde, T. S. Protopsaltis, T. J. Errico, F. J. Schwab, and V. Lafage, "Role of pelvic translation and lower-extremity compensation to maintain gravity line position in spinal deformity," J Neurosurg Spine, vol. 24, no. 3, pp. 436-46, March, 2016.

[7] S. D. Glassman, M. P. Coseo, and L. Y. Carreon, "Sagittal balance is more than just alignment: why PJK remains an unresolved problem," Scoliosis Spinal Disord, vol. 11, pp. 1, 2016.

[8] R. Lafage, F. Schwab, V. Challier, J. K. Henry, J. Gum, J. Smith, R. Hostin, C. Shaffrey, H. J. Kim, C. Ames, J. Scheer, E. Klineberg, S. Bess, D. Burton, V. Lafage, and G. International Spine Study, "Defining Spino-Pelvic Alignment Thresholds: Should Operative Goals in Adult Spinal Deformity Surgery Account for Age?," Spine (Phila Pa 1976), vol. 41, no. 1, pp. 62-8, January, 2016.

[9] J. K. Scheer, V. Lafage, J. S. Smith, V. Deviren, R. Hostin, I. M. McCarthy, G. M. Mundis, D. C. Burton, E. Klineberg, M. Gupta, K. Kebaish, C. I. Shaffrey, S. Bess, F. Schwab, C. P. Ames, and G. International Spine Study, "Maintenance of radiographic correction at 2 years following lumbar pedicle subtraction osteotomy is superior with upper thoracic compared with thoracolumbar junction upper instrumented vertebra," Eur Spine J, vol. 24 Suppl 1, pp. S121-30, January, 2015.

[10] K. J. Cho, S. I. Suk, S. R. Park, J. H. Kim, S. S. Kim, T. J. Lee, J. J. Lee, and J. M. Lee, "Short fusion versus long fusion for degenerative lumbar scoliosis," Eur Spine J, vol. 17, no. 5, pp. 650-6, May, 2008.

[11] M. C. Gupta, E. Ferrero, G. Mundis, J. S. Smith, C. I. Shaffrey, F. Schwab, H. J. Kim, O. Boachie-Adjei, V. Lafage, S. Bess, R. Hostin, D. C. Burton, C. P. Ames, K. Kebaish, E. Klineberg, and G. International Spine Study, "Pedicle Subtraction
Osteotomy in the Revision Versus Primary Adult Spinal Deformity Patient: Is There a Difference in Correction and Complications?," Spine (Phila Pa 1976), vol. 40, no. 22, pp. E1169-75, November, 2015.

[12] R. E. Isaacs, J. Hyde, J. A. Goodrich, W. B. Rodgers, and F. M. Phillips, "A prospective, nonrandomized, multicenter evaluation of extreme lateral interbody fusion for the treatment of adult degenerative scoliosis: perioperative outcomes and complications," Spine (Phila Pa 1976), vol. 35, no. 26 Suppl, pp. S322-30, Dec. 15, 2010.

[13] V. Lafage, F. Schwab, S. Vira, R. Hart, D. Burton, J. S. Smith, O. Boachie-Adjei, A. Shelokov, R. Hostin, C. I. Shaffrey, M. Gupta, B. A. Akbarnia, S. Bess, and J. P. Farcy, "Does vertebral level of pedicle subtraction osteotomy correlate with degree of spinopelvic parameter correction?," J Neurosurg Spine, vol. 14, no. 2, pp. 184-91, February, 2011.

[14] R. Patel, S. N. Khan, M. C. McMains, and M. Gupta, "Technique for Lumbar Pedicle Subtraction Osteotomy for Sagittal Plane Deformity in Revision," Am J Orthop (Belle Mead N.J.), vol. 44, no. 6, pp. 261-4, June, 2015.

[15] A. A. Theologis, G. M. Mundis, Jr., S. Nguyen, D. O. Okonkwo, P. V. Mummaneni, J. S. Smith, C. I. Shaffrey, R. Fessler, S. Bess, F. Schwab, B. G. Diebo, D. Burton, R. Hart, V. Deviren, C. Ames, and G. for the International Spine Study, "Utility of multilevel lateral interbody fusion of the thoracolumbar coronal curve apex in adult deformity surgery in combination with open posterior instrumentation and L5-S1 interbody fusion: a case-matched evaluation of 32 patients," J Neurosurg Spine, pp. 1-12, Oct. 21, 2016.

The invention claimed is:

1. A process operable using a computerized system for providing one or more output images of the spinal region of a subject for which anatomical landmarks applicable for clinical assessment are labeled in a pre-trained neural network for clinical assessment of malalignment of a spine of a subject, the computerized system including an image data acquisition device, a pre-trained neural network and an output module operably interconnected together via a communication link, said process including the steps of:
(i) by an image data acquisition device, acquiring one or more data input sets indicative of the spinal region of a subject, wherein each data input set of the one or more data input sets is indicative of an optical image of said subject at one or more corresponding postures of the subject;
(ii) in a pre-trained neural network, providing labels to anatomical landmarks of said one or more data input sets each of which is indicative of said optical image of the subject at said one or more postures of the subject acquired during step (i) so as to provide one or more optical output images for subsequent clinical assessment of the spine of said subject,
wherein the pre-trained neural network has been pre-trained utilising one or more training data input sets corresponding to one or more predetermined postures of training subjects acquired from a plurality of training subjects,
wherein said one or more predetermined postures are postures utilized for clinical assessment of malalignment of the spine of a subject; wherein the anatomical landmarks of the spine of said one or more training data input sets acquired from said plurality of training subjects have been pre-labeled by at least one clinician; and
wherein the one or more postures of said subject for which the one or more data input sets of the subject acquired during step (i) correspond to one or more of said predetermined postures; and
(iii) displaying by the output module, the one or more optical output images of the spinal region of said subject having said labels provided thereto by the pre-trained neural network, for clinical assessment.

2. The process according to claim 1, wherein the pre-trained neural network is further trained utilising one or more X ray images acquired simultaneously when the one or more data input sets are acquired from the plurality of training subjects, and wherein the neural network provides one or more simulated X ray images corresponding to the one or more acquired data input sets of the spinal region of the subject, having said labels provided thereto by the pre-trained neural network, for clinical assessment.

3. The process according to claim 1, wherein the pre-trained neural network is further trained utilising one or more X ray images acquired simultaneously when the one or more data input sets are acquired from the plurality of training subjects, and wherein the neural network provides one or more simulated X ray images corresponding to the one or more acquired data input sets of the spinal region of said subject, having said labels provided thereto by the pre-trained neural network, and wherein said one or more simulated X ray images corresponding to the one or more acquired optical input images of the spinal region of said subject having said labels provided thereto are processed by a processing module, wherein said processing module provides for image analysis and calculations to the labelled images and provides analysis and clinical assessment of malalignment of a spine of said subject.

4. The process according to claim 1, wherein the image data acquisition device is an optical image acquisition device, and wherein the data input sets are optical input images.

5. The process according to claim 4, wherein the optical image acquisition device is a fixed CCD/CMOS camera installed in clinics or hospitals in a room or environment in which an input image is to be acquired.

6. The process according to any one of claims 4, wherein the optical image acquisition device is a built-in camera of a purpose specific mobile device or a mobile device.

7. The process according to claim 1, wherein the image data acquisition device is a depth sensor, and the depth sensor is preferably a depth camera.

8. The process according to claim 1, wherein the anatomical landmarks of the spine of said one or more training data input sets acquired from said plurality of training subjects have been pre-labeled by two or more clinicians, wherein consensus is sought between said two or more clinicians.

9. The process according to claim 8, wherein in the event consensus is not reached between said two or more clinicians, one or more further clinician pre-labels said one or more training data input sets until a consensus threshold is reached.

10. A process operable using a computerized system for providing one or more output images of the spinal region of a subject for which anatomical landmarks applicable for clinical assessment are labeled for clinical assessment of malalignment of a spine of a subject, the computerized system including an input interface, a pre-trained neural network and an output module operably interconnected together via a communication link, said process including the steps of:
 acquiring one or more medical input images of a subject, wherein each medical input image of the one or more medical input images is an image of said subject at one or more corresponding postures;
 (ii) in a pre-trained neural network, providing labels to anatomical landmarks of one or more medical input images of said subject at said one or more postures of the subject acquired during step (i) for providing one or more medical output images for subsequent clinical assessment of the spine of said subject which are input into a pre-trained neural network by a input interface; wherein the pre-trained neural network has been pre-trained utilising or more medical training images corresponding to one or more predetermined postures of training subjects acquired from a plurality of training subjects at one or more predetermined postures;
 wherein said one or more predetermined postures are postures utilized for clinical assessment of malalignment of the spine of said subject, and wherein the anatomical landmarks of the spine of said one or more medical training images acquired from the plurality of training subjects have been pre-labeled by at least one clinician; and
 wherein the one or more postures of said subject for which the one or more medical input images of the subject acquired during step (i) correspond to one or more of said predetermined postures; and
 (iii) displaying by the output module, the one or more medical output images of the spinal region of said subject having said labels provided thereto by the pre-trained neural network, for clinical assessment.

11. The process according to claim 10, wherein the medical image is selected from the group including CT (computer tomography) scans, X-ray, MRI (magnetic resonance imaging, CBCT (Cone beam computed tomography) or the like.

12. A computerized system for providing one or more images of the region of interest of a subject for which anatomical landmarks applicable for clinical assessment are labeled for clinical assessment of malalignment of a region of interest of a subject, the computerized system including:
 an image data acquisition device, for acquiring one or more data input sets of the region of interest of a subject, wherein each data input set of the one or more data input sets is indicative of an optical image of said subject at one or more corresponding postures of the subject;
 a pre-trained neural network, for providing labels to anatomical landmarks of said one or more data input sets indicative of the subject at said one or more postures of the subject acquired from the image data acquisition device for providing optical output images for subsequent clinical assessment of the bone structure at the region of interest of said subject,
 wherein the pre-trained neural network has been pre-trained one or more training data input sets corresponding to one or more predetermined postures of training subjects acquired from a plurality of training subjects,
 wherein said one or more predetermined postures are postures utilized for clinical assessment of malalignment of the bone structure at the region of interest of a subject; wherein the anatomical landmarks of the bone structure at the region of interest of said one or more training data input sets acquired from said plurality of training subjects have been pre-labeled by at least one clinician and;
 wherein the one or more postures of said subject for which the one or more data input sets indicative of the subject is acquired correspond to one or more of said predetermined postures; and
 an output module, for displaying the one or more optical output images of the region of interest of said subject having said labels provided thereto by the pre-trained neural network, for clinical assessment.

13. A computerized system for providing one or more images of the region of interest of a subject for which anatomical landmarks applicable for clinical assessment are labeled for subsequent clinical assessment of malalignment of a bone structure at the region of interest of a subject, the computerized system including:
 an input interface for receiving one or more medical input images of a subject, wherein each medical input image of the one or more medical input images is an image of said subject at one or more corresponding postures,
 a pre-trained neural network for providing labels to anatomical landmarks of one or more medical input images of said subject at said one or more postures of said subject received from the input interface, and for providing one or more medical output images for subsequent clinical assessment of the bone structure at the region of interest of said subject which are input into the pre-trained neural network by a input interface;

wherein the pre-trained neural network has been pre-trained utilising or more medical training images corresponding to one or more predetermined postures of training subjects acquired from a plurality of training subjects at one or more predetermined postures wherein said one or more predetermined postures are postures utilized for clinical assessment of malalignment of the bone structure at the region of interest of said subject, and wherein the anatomical landmarks of the bone structure at the region of interest of said one or more medical training images acquired from the plurality of training subjects have been pre-labeled by a clinician; and wherein the one or more postures of said subject for which the one or more medical input images of the subject acquired correspond to one or more of said predetermined postures; and an output module for displaying the one or more medical output images of the region of interest of said subject having said labels provided thereto by the pre-trained neural network, for clinical assessment.

14. The system according to claim 13, further including an image data acquisition device, for acquiring said one or more medical input images of said subject.

15. The system according to claim 12, wherein the image data acquisition device is an optical image acquisition device, and wherein the data input sets are optical input images.

16. The system according to claim 12, wherein the optical image acquisition device is a fixed CCD/CMOS camera installed in clinics or hospitals in a room or environment in which the image is to be acquired; or the optical image acquisition device is a built-in camera of a purpose specific mobile device or a mobile device.

17. The system according to claim 12, wherein the image data acquisition device is a depth sensor, wherein the depth sensor is preferably a depth camera.

18. The system according to claim 12, wherein the optical image acquisition device further includes an output module, wherein the output module is preferably a visual display unit.

19. The system according to claim 12, wherein said optical image acquisition device carries thereon a software executable thereon for communication with said neural network.

20. The system according to claim 12, wherein the optical image acquisition device includes a user interface for guiding a user in respect of acquisition of said predetermined postures and the acquisition of images thereof.

* * * * *